(12) United States Patent
Mitarai et al.

(10) Patent No.: US 12,009,063 B2
(45) Date of Patent: Jun. 11, 2024

(54) QUANTUM INFORMATION PROCESSING METHOD AND DEVICE FOR FINDING A DIFFERENTIAL OF ENERGY

(71) Applicant: QUNASYS INC., Tokyo (JP)

(72) Inventors: Kosuke Mitarai, Tokyo (JP); Yuya Nakagawa, Tokyo (JP)

(73) Assignee: QUNASYS INC., Tokyo (JP)

( * ) Notice: Subject to any disclaimer, the term of this patent is extended or adjusted under 35 U.S.C. 154(b) by 629 days.

(21) Appl. No.: 17/159,954

(22) Filed: Jan. 27, 2021

(65) Prior Publication Data

US 2021/0183476 A1 Jun. 17, 2021

Related U.S. Application Data

(63) Continuation of application No. PCT/JP2020/019008, filed on May 12, 2020.

(30) Foreign Application Priority Data

May 13, 2019 (JP) ................. 2019-090332

(51) Int. Cl.
    *G06F 11/30* (2006.01)
    *G06F 17/16* (2006.01)
    *G06N 10/20* (2022.01)
    *G06N 10/60* (2022.01)
    *G16C 10/00* (2019.01)

(52) U.S. Cl.
    CPC ............. *G16C 10/00* (2019.02); *G06F 17/16* (2013.01); *G06N 10/20* (2022.01); *G06N 10/60* (2022.01)

(58) Field of Classification Search
    CPC ........ G16C 10/00; G16C 20/30; G16C 20/90; G06N 10/00; G06N 10/20; G06N 10/60; G06F 17/16
    See application file for complete search history.

(56) References Cited

U.S. PATENT DOCUMENTS

2020/0065439 A1  2/2020  Babbush et al.

OTHER PUBLICATIONS

Romero et al., Strategies for Quantum Computing Molecular Energies Using the Unitary Coupled Cluster Ansatz, Published: Oct. 19, 2018, Quantum Sci. Technol. 4, 22 pp. (Year: 2018).*

(Continued)

*Primary Examiner* — Phuong Huynh
(74) *Attorney, Agent, or Firm* — Brooks Kushman P.C.

(57) ABSTRACT

A classical computer outputs a Hamiltonian and initial information of a parameter expressing a quantum circuit. The classical computer, according to a parameter expressing a first quantum circuit that was output from a quantum computer and was generated by quantum computation employing a Variational Quantum Eigensolver (VQE) based on the Hamiltonian and the initial information, generates a parameter expressing a second quantum circuit including a rotation gate and outputs the parameter expressing the second quantum circuit. The classical computer, based on measurement results of quantum computation that were output from the quantum computer and computed according to the parameter expressing the second quantum circuit, based on the Hamiltonian, and based on a derivative function of the Hamiltonian, generates a derivative function of energy corresponding to the Hamiltonian and outputs the derivative function of energy.

13 Claims, 6 Drawing Sheets

(56) References Cited

OTHER PUBLICATIONS

A variational eigenvalue solver on a photonic quantum processor, by A. Peruzzo, J. McClean, P. Shadbolt, M.-H. Yung, X.-Q. Zhou, P. J. Love, A. Aspuru-Guzik and J. L.O'Brien; Nature Communications,5, article No. 4213, 2014.

Quantum algorithm for molecular properties and geometry optimization, by I. Kassal and A. Aspuru-Guzik; J. Chem. Phys. 131, 224102 (2009).

Efficient Variational Quantum Simulator Incorporating Active Error Minimization, by Y. Li and S. C. Benjamin; Phys. Rev. X 7, 021050 (2017).

Quantum circuit learning, by K Mitarai, M Negoro, M Kitagawa, K Fujii; Physical Review A 98, 032309, 2018.

Subspace-search variational quantum eigensolver for excited states, by K. M. Nakanishi, K. Mitarai, and K. Fujii; (2018), arXiv:1810.09434.

Variational quantum algorithms for discovering Hamiltonian spectra, by S. Endo, T. Jones, S. McArdle, X. Yuan, and S. Benjamin; (2018), arXiv:1806.05707.

Variational Quantum Computation of Excited States, by O. Higgott, D. Wang, and S. Brierley; (2018), arXiv:1805.08138.

Hybrid quantum-classical hierarchy for mitigation of decoherence and determination of excited states, by J. R. McClean, M. E. Kimchi-Schwartz, J. Carter, and W. A. de Jong; Phys. Rev. A 95, 042308 (2017).

PySCF: the Python-based simulations of chemistry framework, Q. Sun, T. C. Berkelbach, N. S. Blunt, G. H. Booth, S. Guo, Z. Li, J. Liu, J. D. McClain, E. R. Sayfutyarova, S. Sharma, S.Wouters, and G. K. Chan; Wiley Interdisciplinary Reviews: Computational Molecular Science 8, e1340 (2017).

OpenFermion: The Electronic Structure Package for Quantum Computers, by J. R. McClean, K. J. Sung, I. D. Kivlichan, Y. Cao, C. Dai, E. S. Fried, C. Gidney, B. Gimby, P. Gokhale, T. Hner, T. Hardikar, V. Havlek, O. Higgott, C. Huang, J. Izaac, Z. Jiang, X. Liu, S. McArdle, M. Neeley, T. O'Brien, B. O'Gorman, I. Ozdan, M. D. Radin, J. Romero, N. Rubin, N. P. D. Sawaya, K. Setia, S. Sim, D. S. Steiger, M. Steudtner, Q. Sun, W. Sun, D. Wang, F. Zhang, and R. Babbush, ; (2017), arXiv:1710.07629.

Strategies for quantum computing molecular energies using the unitary coupled cluster ansatz, by Jonathan Romero, Ryan Babbush, Jarrod R. McClean, Cornelius Hempel, Peter Love, Alán Aspuru-Guzik; (2018), arXiv:1701.02691.

Methodology for replacing indirect measurements with direct measurements, by Kosuke Mitarai, Keisuke Fujii; (2019), arXiv:1901.00015.

Japanese Office Action dated Aug. 7, 2020 for related Japanese Patent Application No. 2019-090332.

Japanese Written Opinion dated May 12, 2020 for related international Patent Application PCT/JP2020/019008.

Extended European Search Report of European patent application No. 20806807.2 dated Dec. 23, 2022, 10 pages.

Kosuke et al., "Theory of analytical energy derivatives for the variational quantum eigensolver", Physical Review Research, vol. 2, No. 1, May 10, 2019 (May 10, 2019), XP093005379.

* cited by examiner

FIG.3

$|0\rangle^{\otimes n}$ — $U_{b:1}$ — $R_{b,\nu}^{\pm}$ — $U_{a:b+1}$ — $R_{a,\mu}^{\pm}$ — $U_{N:a+1}$ — $\langle Q \rangle_{(a,\mu,\pm),(b,\nu,\pm)}$

QUANTUM INFORMATION PROCESSING METHOD AND DEVICE FOR FINDING A DIFFERENTIAL OF ENERGY

CROSS-REFERENCE TO RELATED APPLICATIONS

This application is a continuation application of international application Serial No. PCT/JP2020/019008 filed May 12, 2020, which, in turn, claims priority to Japanese application Serial No. 2019-090332 filed May 13, 2019, the disclosures of which are hereby incorporated in their entirety by reference herein

TECHNICAL FIELD

Technology disclosed herein relates to a quantum information processing method for finding a differential of energy, and to a classical computer, a quantum computer, a hybrid system, and a recording medium.

BACKGROUND

Document 1 ("A Variational Eigenvalue Solver on a Photonic Quantum Processor" by A. Peruzzo, J. McClean, P. Shadbolt, M-H. Yung, X-Q. Zhou, P. J. Love, A. Aspuru-Guzik and J. L. O'Brien in Nature Communications 5 Article number 4213 (2014)) discloses a variational-quantum eigensolver (referred to hereafter simply as VQE). The VQE is employed to compute an approximation of an eigenvalue for minimum of a Hamiltonian by variational updating of a parameter of a quantum circuit. Energy information corresponding to the eigenvalue of the minimum of the Hamiltonian is useful information in, for example, quantum chemistry calculations.

In quantum chemistry calculations, it is common to define several non-time-dependent physical properties or chemical properties using derivative functions of energy. Regarding this point, Document 2 ("Quantum Algorithm for Molecular Properties and Geometry Optimization" by I. Kassal and A. Aspuru-Guzik in Journal of Chemical Physics 131, 224102 (2009)) discloses technology for calculating derivative functions of energy by using quantum computations by a quantum computer to perform quantum phase estimations.

Related Non Patent Document

Non Patent Document 1: "A Variational Eigenvalue Solver on a Photonic Quantum Processor" by A. Peruzzo, J. McClean, P. Shadbolt, M-H. Yung, X-Q. Zhou, P. J. Love, A. Aspuru-Guzik and J. L. O'Brien in Nature Communications 5 Article number 4213 (2014)

Non Patent Document 2: "Quantum Algorithm for Molecular Properties and Geometry Optimization" by I. Kassal and A. Aspuru-Guzik in Journal of Chemical Physics 131, 224102 (2009)

SUMMARY

A first aspect of the present disclosure is a quantum information processing method for finding a differential of energy by processing executed on a hybrid system including a classical computer and a quantum computer. The quantum information processing method includes: the classical computer outputting a Hamiltonian and initial information of a parameter expressing a quantum circuit; the quantum computer, based on the Hamiltonian and the initial information output from the classical computer, executing quantum computation employing a Variational Quantum Eigensolver (VQE) to generate a parameter expressing a first quantum circuit for computing energy, and outputting the parameter expressing the first quantum circuit; the classical computer, based on the parameter expressing the first quantum circuit output from the quantum computer, generating a parameter expressing a second quantum circuit including a rotation gate, and outputting the parameter expressing the second quantum circuit; the quantum computer, based on the parameter expressing the second quantum circuit output from the classical computer, executing quantum computation and outputting measurement results of this quantum computation; and the classical computer, based on the measurement results output from the quantum computer, the Hamiltonian, and a derivative function of the Hamiltonian, computing a derivative function of energy corresponding to the Hamiltonian and outputting the derivative function of energy.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF THE DRAWINGS

FIG. 3 is a schematic diagram illustrating an example of a second quantum circuit.

DETAILED DESCRIPTION

Detailed explanation follows regarding an exemplary embodiment of technology disclosed herein, with reference to the drawings.

First Exemplary Embodiment: Hybrid System 100

Figure 1:
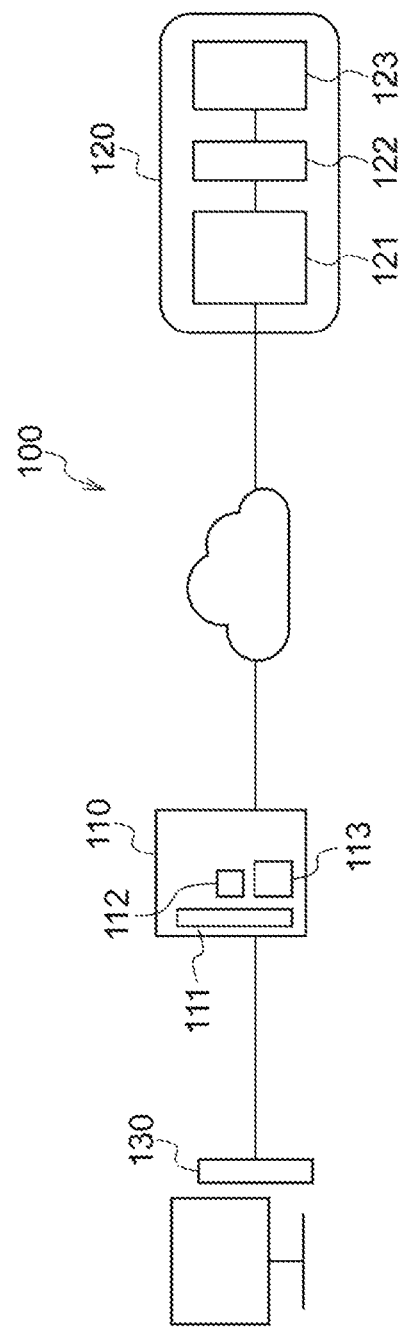
FIG. 1 is a diagram illustrating an example of a schematic configuration of a hybrid system 100 of an exemplary embodiment.

FIG. 1 illustrates a hybrid system 100 according to a first exemplary embodiment. The hybrid system 100 of the present exemplary embodiment includes a classical computer 110, a quantum computer 120, and a user terminal 130. As illustrated in FIG. 1, the classical computer 110, the quantum computer 120, and the user terminal 130 are, for example, connected together over a computer network such as an IP network.

In the hybrid system 100 of the present exemplary embodiment, the quantum computer 120 performs prescribed quantum computations in response to requests from the classical computer 110, and then outputs the computation results of such quantum computations to the classical computer 110. The classical computer 110 then outputs the computation results for the quantum computations to the user terminal 130. Prescribed computation processing is accordingly executed by the hybrid system 100 as a whole.

The classical computer 110 includes a communication section 111 such as a communication interface, a processing section 112 such as a processor, a central processing unit (CPU), or the like, and an information storage section 113 including a storage device such as memory or a hard disk, or a storage medium. The classical computer 110 is configured to perform various processing by executing a program. The classical computer 110 may include one or plural devices or servers. The program may be one program, or may include plural programs, and may be configured as a non-transitory program product recorded on a computer-readable storage medium.

As an example, based on information transmitted from the classical computer 110, the quantum computer 120 generates an electromagnetic wave for irradiating at least one qubit out of a qubit cluster 123. The quantum computer 120 then executes the quantum circuit by at least one qubit out of the qubit cluster 123 being irradiated with the generated electromagnetic wave.

In the example illustrated in FIG. 1, the quantum computer 120 includes a control device 121 to perform communication with the classical computer 110, an electromagnetic wave generation device 122 to generate electromagnetic waves in response to requests from the control device 121, and the qubit cluster 123 subjected to irradiation of electromagnetic waves from the electromagnetic wave generation device 122. Note that in the present exemplary embodiment, the "quantum computer" refers to a computer that performs at least some computation with qubits, rather than denoting a computer that does not perform any computation using classical bits at all.

The control device 121 is a classical computer that performs computation using classical bits, and may also perform some or all of the processing that is described in the present specification as being performed by the classical computer 110, on behalf thereof. For example, the control device 121 may be stored in advance with, or decide, a quantum circuit, and may generate quantum gate information to execute a quantum circuit $U(\theta)$ on the qubit cluster 123 in response to receipt of a parameter $\theta$ for the quantum circuit $U(\theta)$.

The user terminal 130 is a classical computer that performs computation using classical bits. The user terminal 130 receives information input by a user, and executes processing in response to this information.

Figure 2:
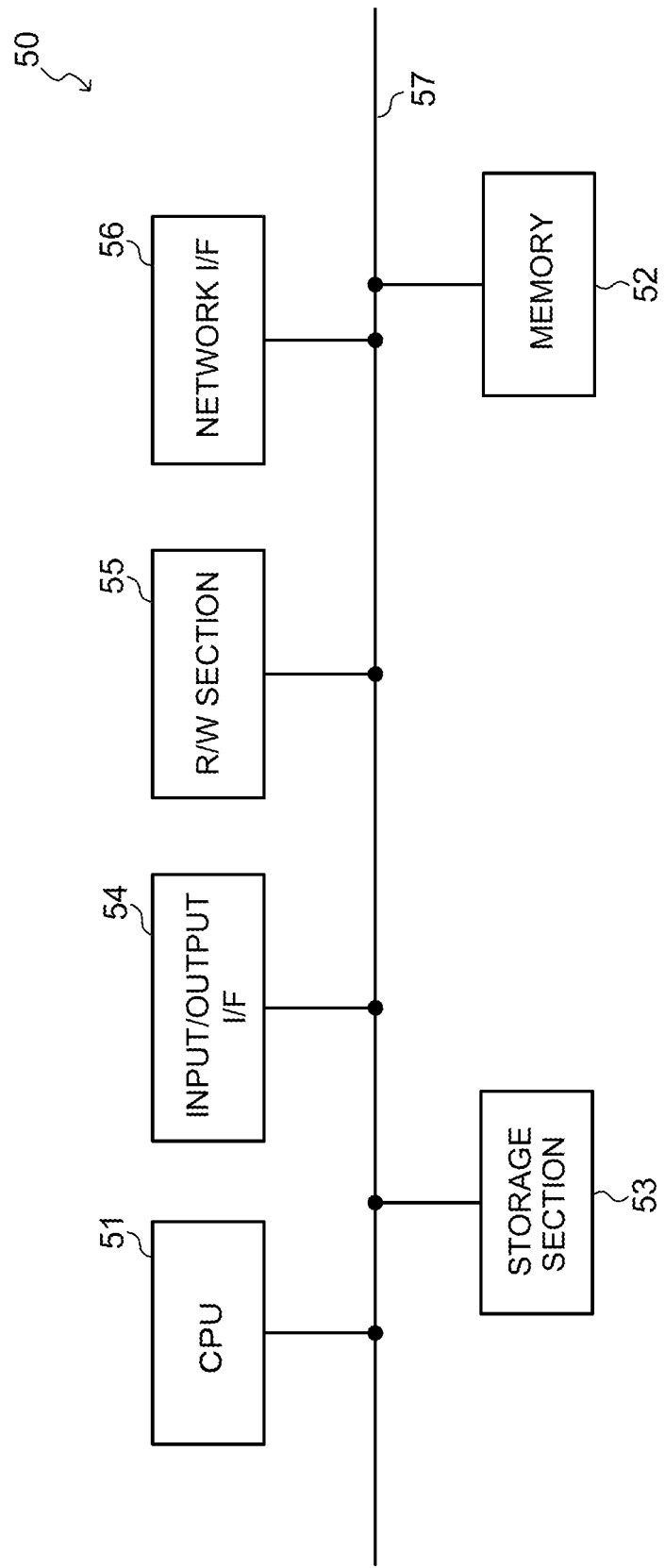
FIG. 2 is a schematic block diagram illustrating a computer that may function as a classical computer 110, a control device 121, or a user terminal 130.

The classical computer 110, the control device 121, and the user terminal 130 may, for example, be implemented by a computer 50, illustrated in FIG. 2. The computer 50 includes a CPU 51, memory 52 serving as a temporarily storage region, and a non-volatile storage section 53. The computer 50 further includes an input/output interface (I/F) 54 connected to an external device, an output device, or the like, and a read/write (R/W) section 55 that controls the reading and writing of data to a recording medium 59. The computer 50 further includes a network I/F 56 for connection to a network such as the internet. The CPU 51, the memory 52, the storage section 53, the input/output I/F 54, the R/W section 55, and the network I/F 56 are connected together through a bus 57.

The hybrid system 100 of the first exemplary embodiment computes a derivative function of energy for a ground state. Explanation follows regarding the following assumptions.

VQE

First, brief explanation follows regarding a VQE algorithm.

The quantum computer executes quantum computations based on the quantum circuit $U(\theta)$. A relationship between the quantum circuit $U(\theta)$ and a quantum state $|\psi(\theta)\rangle$ is expressed by the following equation. Note that $\psi(\theta)$ represents a wave function.

$$|\psi(\theta)\rangle = U(\theta)|0\rangle^{\otimes n}$$

Note that the term of the following equation represents an n [qubit] initialized state.

$$|0\rangle^{\otimes n}$$

As indicated by the expression below, $\theta$ is an N-dimensional parameter vector expressing a quantum circuit. Hereafter, $\theta_p$ (p=a, b, c, . . . ) represents elements of the parameter vectors $\theta$ for the quantum circuit $U(\theta)$. The parameter $\theta$ for the quantum circuit $U(\theta)$ is information expressing a configuration of a quantum circuit. The quantum computer executes quantum computations according to the parameter $\theta$ on the quantum circuit $U(\theta)$.

$$\theta \in \mathbb{R}^N$$

A VQE optimizes the parameter $\theta$ for the quantum circuit $U(\theta)$ so as to minimize energy $E(\theta) = \langle\psi(\theta)|H|\psi(\theta)\rangle$ for a given Hamiltonian H. Note that the following Equation (1) is satisfied for all a in an optimal parameter $\theta$ for the quantum circuit $U(\theta)$.

$$\frac{\partial E(\theta)}{\partial \theta_a} = 0, \tag{1}$$

Note that the optimal parameter for the quantum circuit $U(\theta)$ is denoted $\theta^*$. Adopting the expression of Equation (2) below enables Equation (1) can be expressed using Equation (3) below.

$$|\partial_a \psi(\theta)\rangle = \frac{\partial}{\partial \theta_a}|\psi(\theta)\rangle, \tag{2}$$

$$Re\langle\psi(\theta^*)|H|\partial_a\psi(\theta^*)\rangle = 0. \tag{3}$$

A high order partial derivative function of the wave function $w(\theta)$ with respect to the parameter $\theta$ for the quantum circuit $U(\theta)$ is expressed by Equation (4) below.

$$|\partial_a \partial_b \cdots \partial_c \psi(\theta)\rangle = \frac{\partial}{\partial \theta_a}\frac{\partial}{\partial \theta_b}\cdots\frac{\partial}{\partial \theta_c}|\psi(\theta)\rangle, \tag{4}$$

Many non-time dependent physical characteristics or chemical characteristics are computed based on derivative functions of energy with respect to a parameter x, which expresses states of a system. The system-state-parameter x is, for example, a parameter expressing an electric field, magnetic field, positional coordinates of an atomic nucleus, or the like for the system. In the present exemplary embodiment, the system-state-parameter x is expressed by an M-dimensional vector as in the following equation. Note that $x_q$ (q=i, j, k, . . . ) represents elements of the parameter vector x, which expresses the system states.

$$x \in \mathbb{R}^M$$

The Hamiltonian H and an optimal parameter $\theta^*$ for the quantum circuit $U(\theta)$ are functions of the system-stateparameter x. The Hamiltonian H is thus expressed as H(x). Moreover, the optimal parameter θ* of the quantum circuit U (θ) is expressed as θ*(x). The energy E of the system is thus expressed by Equation (5) below.

$$E(\theta, x) = \langle \psi(\theta) | H(x) | \psi(\theta) \rangle. \qquad (5)$$

Note that E*(x)=E* (θ* (x), x), wherein E*(x) denotes the energy of the ground state. In the present exemplary embodiment, a derivative function of E* (θ* (x), x) with respect to the system-state-parameter x is computed as indicated in the equations below.

$$\frac{\partial E^*(x)}{\partial x_i}$$

$$\frac{\partial}{\partial x_i} \frac{\partial E^*(x)}{\partial x_j}$$

$$\frac{\partial}{\partial x_i} \frac{\partial}{\partial x_j} \frac{\partial E^*(x)}{\partial x_k}$$

Analytical Expression of Derivative Functions

Next, explanation follows regarding analytical expression of derivative functions of energy. Derivative functions for the energy of the ground state are expressed by Equation (6) to Equation (8) below.

$$\frac{\partial E^*(x)}{\partial x_i} = \left\langle \psi(\theta^*(x), x) \left| \frac{\partial H(x)}{\partial x_i} \right| \psi(\theta^*(x), x) \right\rangle, \qquad (6)$$

$$\frac{\partial}{\partial x_i} \frac{\partial E^*(x)}{\partial x_j} = \qquad (7)$$

$$\sum_a \frac{\partial \theta_a^*(x)}{\partial x_i} \frac{\partial}{\partial \theta_a} \frac{\partial E(\theta^*(x), x)}{\partial x_j} + \left\langle \psi(\theta^*(x)) \left| \frac{\partial}{\partial x_i} \frac{\partial H(x)}{\partial x_j} \right| \psi(\theta^*(x)) \right\rangle,$$

$$\frac{\partial}{\partial x_i} \frac{\partial}{\partial x_j} \frac{\partial E^*(x)}{\partial x_k} = \sum_{a,b,c} \frac{\partial}{\partial \theta_a} \frac{\partial}{\partial \theta_b} \frac{\partial E(\theta^*(x), x)}{\partial \theta_c} \frac{\partial \theta_a^*(x)}{\partial x_i} \frac{\partial \theta_b^*(x)}{\partial x_j} \frac{\partial \theta_c^*(x)}{\partial x_k} + \qquad (8)$$

$$\left\langle \psi(\theta^*(x)) \left| \frac{\partial}{\partial x_i} \frac{\partial}{\partial x_j} \frac{\partial E^*(x)}{\partial x_k} \right| \psi(\theta^*(x)) \right\rangle +$$

$$\sum_{a,b} \left[ \frac{\partial \theta_a^*(x)}{\partial x_i} \frac{\partial \theta_b^*(x)}{\partial x_j} \frac{\partial}{\partial \theta_b} \frac{\partial}{\partial \theta_a} \frac{\partial E(\theta^*(x), x)}{\partial x_k} + \frac{\partial \theta_a^*(x)}{\partial x_k} \frac{\partial \theta_b^*(x)}{\partial x_i} \right.$$

$$\left. \frac{\partial}{\partial \theta_b} \frac{\partial}{\partial \theta_a} \frac{\partial E(\theta^*(x), x)}{\partial x_j} + \frac{\partial \theta_a^*(x)}{\partial x_j} \frac{\partial \theta_b^*(x)}{\partial x_k} \frac{\partial}{\partial \theta_b} \frac{\partial}{\partial \theta_a} \frac{\partial E(\theta^*(x), x)}{\partial x_i} \right] +$$

$$\sum_a \left[ \frac{\partial \theta_a^*(x)}{\partial x_i} \frac{\partial}{\partial \theta_a} \frac{\partial}{\partial x_j} \frac{\partial E(\theta^*(x), x)}{\partial x_k} + \right.$$

$$\left. \frac{\partial \theta_a^*(x)}{\partial x_k} \frac{\partial}{\partial \theta_a} \frac{\partial}{\partial x_i} \frac{\partial E(\theta^*(x), x)}{\partial x_j} + \frac{\partial \theta_a^*(x)}{\partial x_j} \frac{\partial}{\partial \theta_a} \frac{\partial}{\partial x_k} \frac{\partial E(\theta^*(x), x)}{\partial x_i} \right],$$

Note that Equation (6) to Equation (8) above assume the following equation.

$$\frac{\partial E(\theta^*(x), x)}{\partial \theta} = 0.$$

Moreover, partial derivative functions with respect to parameter x of the optimal parameter θ* (x) are found by solving Equation (9) and Equation (10) below.

$$\sum_b \frac{\partial}{\partial \theta_a} \frac{\partial E(\theta^*(x), x)}{\partial \theta_b} \frac{\partial \theta_b^*(x)}{\partial x_i} = -\frac{\partial}{\partial \theta_a} \frac{\partial E(\theta^*(x), x)}{\partial x_i}, \qquad (9)$$

$$\sum_b \frac{\partial}{\partial \theta_a} \frac{\partial E(\theta^*(x), x)}{\partial \theta_b} \frac{\partial}{\partial x_i} \frac{\partial \theta_b^*(x)}{\partial x_j} = -\gamma_a^{(ij)}(\theta^*(x), x), \qquad (10)$$

γ in Equation (10) above can be expressed by Equation (11) below.

$$\gamma_c^{(ij)} = \qquad (11)$$

$$\sum_{a,b} \frac{\partial}{\partial \theta_c} \frac{\partial}{\partial \theta_a} \frac{\partial E}{\partial \theta_b} \frac{\partial \theta_a^*}{\partial x_i} \frac{\partial \theta_b^*}{\partial x_j} + 2 \sum_a \frac{\partial}{\partial \theta_c} \frac{\partial}{\partial \theta_a} \frac{\partial E}{\partial x_j} \frac{\partial \theta_a^*}{\partial x_i} + \frac{\partial}{\partial \theta_c} \frac{\partial}{\partial x_i} \frac{\partial E}{\partial x_j}.$$

Computation of Ground State Derivative Function and Measurement Thereof

The hybrid system 100 of the present exemplary embodiment is a system that operates in n[qubits]. The Hamiltonian H can be decomposed into a sum of Pauli operators I, X, Y, Z included in the Pauli operator collection of the following equation.

$$\mathcal{P} = \{I, X, Y, Z\}^{\otimes n}$$

Accordingly, the Hamiltonian H can be expressed by Equation (12) below.

$$H(x) = \sum_{P \in \mathcal{P}} h_P(x) P, \qquad (12)$$

Note that $h_P(x)$ in Equation (12) is a coefficient expressed by the following equation.

$$h_P(x) \in \mathbb{R}$$

In order to compute derivative functions of energy, it is necessary to compute the derivative function of the Hamiltonian H such as in Equations (13) below.

$$\frac{\partial H(x)}{\partial x_i} \qquad (13)$$

$$\frac{\partial}{\partial x_i} \frac{\partial H(x)}{\partial x_j}$$

$$\frac{\partial}{\partial x_i} \frac{\partial}{\partial x_j} \frac{\partial H(x)}{\partial x_k}$$

Derivative functions of Hamiltonian H such as expressed by Equations (13) are computable using a classical computer. Note that the computations in Equations (13) correspond to the derivative functions of $h_P(x)$ in Equation (12) above.

Notation for Expressing a Quantum Circuit

Next, explanation follows regarding a notation for expressing a quantum circuit. Note that in the present exemplary embodiment, the quantum circuit U (θ) is expressed as a product of unitary matrices as in Equation (14) below.

$$U(\theta) = U_N(\theta hd\ N) \ldots U_2(\theta_2) U_1(\theta_1). \qquad (14)$$

Each unitary matrix $U_a(\theta_a)$ is generated by a generator $G_a$ of the following equation. Note that i represents an imaginary number therein.

$$U_a = e^{i\theta_a G_a}$$

The generator $G_a$ mentioned above can be expressed by Equation (15) below.

$$G_a = \sum_\mu g_{a,\mu} P_{a,\mu},$$

$$g_{a,\mu} \in \mathbb{R} \text{ and } P_{a,\mu} \in \mathcal{P}. \tag{15}$$

Second Order Partial Derivative Function Measurement

Next, explanation follows regarding measurement of a second order partial derivative function of energy E with respect to parameter θ for the quantum circuit U (θ).

In order to find the derivative function of energy E with respect to the system-state-parameter x, it is necessary to obtain information relating to the derivative function of energy E with respect to parameter θ for the quantum circuit U (θ), such as in the equations below.

$$\frac{\partial}{\partial \theta_a} \frac{\partial}{\partial \theta_b} \cdots \frac{\partial E}{\partial \theta_c}$$

$$\frac{\partial}{\partial \theta_a} \frac{\partial}{\partial \theta_b} \cdots \frac{\partial}{\partial \theta_c} \frac{\partial E}{\partial x_i}$$

Note that a first order partial derivative function of energy E with respect to parameter θ for the quantum circuit U (θ), as in the following equation, is computable using the technology disclosed in Reference Document 1 ("Efficient Variational Quantum Simulator Incorporating Active Error Minimization" by Y. Li and S. C. Benjamin in Physical Review X 7, 021050 (2017)) and in Reference Document 2 ("Quantum Circuit Learning" by K. Mitarai, M. Negoro, M. Kitagawa, and K. Fujii in Physical Review A 98, 032309 (2018)).

$$\frac{\partial E}{\partial \theta_a}$$

Thus explanation follows regarding computation of the second order partial derivative function of energy E with respect to parameter θ for the quantum circuit U (θ), as in the following equation.

$$\frac{\partial}{\partial \theta_a} \frac{\partial E}{\partial \theta_b}$$

The second order partial derivative function above can be expressed by Equation (16) below.

$$\frac{\partial}{\partial \theta_a} \frac{\partial E(\theta^*(x), x)}{\partial \theta_b} = \tag{16}$$

$$2\text{Re}[\langle \partial_a \partial_b \psi(\theta^*(x)) | H(x) | \psi(\theta^*(x)) \rangle + \langle \partial_a \psi(\theta^*(x)) | H(x) | \partial_b \psi(\theta^*(x)) \rangle].$$

In Equation (16), $|\partial_a \psi(\theta)\rangle$ can be expressed by Equation (17) below.

$$|\partial_a \psi(\theta)\rangle = i\sum_\mu g_{a,\mu} U_N(\theta_N) \ldots P_{a,\mu} U_a(\theta_a) \ldots U_2(\theta_2) U_1(\theta_1) |0\rangle^{\otimes n}, \tag{17}$$

Moreover, in Equation (16), $|\partial_a \partial_b \psi(\theta)\rangle$ can be expressed by Equation (18) below.

$$|\partial_a \partial_b \psi(\theta)\rangle = -\sum_{\mu,\nu} g_{a,\mu} g_{b,\nu} U_N(\theta_N) \ldots \tag{18}$$

$$P_{a,\mu} U_a(\theta_a) \ldots P_{b,\nu} U_b(\theta_b) \ldots U_2(\theta_2) U_1(\theta_1) |0\rangle^{\otimes n}.$$

Wherein the definition expressed by Equation (19) below applies.

$$|\phi_{(a,\mu),(b,\nu),\ldots,(c,\rho)}(\theta)\rangle := U_N(\theta_N) \ldots (iP_{a,\mu})$$
$$U_a(\theta_a) \ldots (iP_{b,\nu}) U_b(\theta_b) \ldots (iP_{c,\rho}) U_c(\theta_c) \ldots$$
$$U_1(\theta_1) |0\rangle^{\otimes n}. \tag{19}$$

Equation (20) below is satisfied.

$$\frac{\partial}{\partial \theta_a} \frac{\partial E(\theta^*(x), x)}{\partial \theta_b} = 2\sum_{\mu,\nu} \sum_{Q \in \mathcal{P}} h_Q(x) g_{a,\mu} g_{b,\nu} \tag{20}$$

$$\text{Re}[\langle \phi_{(a,\mu),(b,\nu)}(\theta^*(x)) | Q | \psi(\theta^*(x)) \rangle + \langle \phi_{(a,\mu)}(\theta^*(x)) | Q | \phi_{(b,\nu)}(\theta^*(x)) \rangle].$$

FIG. 3 is an explanatory diagram to explain a quantum circuit of the present exemplary embodiment. The quantum circuit illustrated in FIG. 3 is a quantum circuit used to compute the second order partial derivative function of energy E with respect to parameter θ for the quantum circuit U (θ), as represented by Equation (20).

Note that the following equation is satisfied for U in the quantum circuit illustrated in FIG. 3.

$$U_{a:b} = U_a \ldots U_{b+1} U_b$$

$R^\pm_{a,\mu}$ and $R^\pm_{b,\nu}$ of FIG. 3 represent rotation gates. The rotation gates $R^\pm_{a,\mu}$ and $R^\pm_{b,\nu}$ can be expressed by Equation (21) below. Note that "±" appearing as a suffix in the following equations is a symbol determined by parity.

$$R_{a,\mu}^\pm = \exp(\pm i\pi P_{a,\mu}/4)$$

$$R_{b,\nu}^\pm = \exp(\pm i\pi P_{a,\nu}/4) \tag{21}$$

Note that a and b in Equation (21) are indices used to discriminate between elements of the parameter θ for the quantum circuit U (θ) as in Equation (15) and the like. μ in Equation (21) is an index relating to the generator to generate unitary $U_a$ as in Equation (15) and the like.

In the present exemplary embodiment, the quantum computer 120 measures the quantity expressed in the following equation based on the quantum circuit illustrated in FIG. 3.

$$\langle Q \rangle_{\mathbb{R}_{(a,\mu,\pm),(b,\nu,\pm)}}$$

The terms in the following equation that are present in Equation (20) above are computable by quantum computation with the quantum computer 120, and the results thereof are measured.

$$2\text{Re}[\langle \phi_{(a,\mu),(b,\nu)}(\theta^*(x)) | Q | \psi(\theta^*(x)) \rangle + \langle \phi_{(a,\mu)}$$
$$(\theta^*(x)) | Q | \phi_{(b,\nu)}(\psi^*(x)) \rangle] = \langle Q \rangle_{(a,\mu,+),(b,\nu,+)} +$$
$$\langle Q \rangle_{(a,\mu,-),(b,\nu,-)} - \langle Q \rangle_{(a,b,-),(b,\nu,+)} -$$
$$\langle Q \rangle_{a,\mu,+),(b,\nu,-)}. \tag{22}$$

The second order partial derivative function of the energy E found in Equation (20) is accordingly obtained based on the computation results of the quantum computation in Equation (22).

Third Order Partial Derivative Function Measurement

Next, explanation follows regarding measurement of a third order partial derivative function of energy E with respect to parameter θ for the quantum circuit U (θ).

The third order partial derivative function of energy E with respect to parameter θ for the quantum circuit U (θ) can be expressed by Equation (23) below.

$$\frac{\partial}{\partial \theta_d} \frac{\partial}{\partial \theta_b} \frac{\partial E(\theta^*(x), x)}{\partial \theta_c} = 2 \sum_{\mu,\nu,\rho} \sum_{Q \in \mathcal{P}} h_Q(x) g_{a,\mu} g_{b,\nu} g_{c,\rho} \quad (23)$$

$$\mathrm{Re}[\langle \phi_{(a,\mu),(b,\nu),(c,\rho)}(\theta^*(x))|Q|\psi(\theta^*(x))\rangle + \langle \phi_{(a,\mu),(b,\nu)}(\theta^*(x))|Q|\phi_{(c,\rho)}(\theta^*(x))\rangle +$$

$$\langle \phi_{(a,\mu),(c,\rho)}(\theta^*(x))|Q|\phi_{(b,\nu)}(\theta^*(x))\rangle + \langle \phi_{(b,\nu),(c,\rho)}(\theta^*(x))|Q|\phi_{(a,\mu)}(\theta^*(x))\rangle].$$

Figure 4:
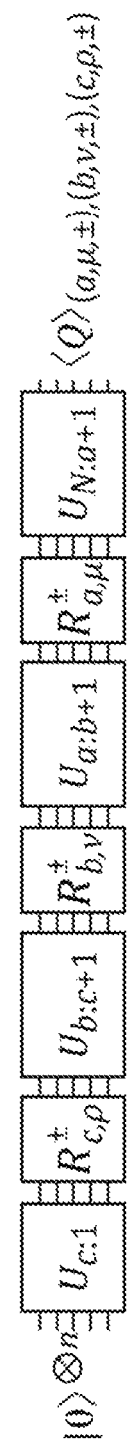
FIG. 4 is a schematic diagram illustrating an example of a second quantum circuit.

FIG. 4 illustrates a quantum circuit for computing the third order partial derivative function of energy E with respect to parameter θ for the quantum circuit U (θ). Note that $R^{\pm}_{c,\rho}$ in FIG. 4 can be expressed by the following equation.

$$R_{c,\rho}^{\pm} = \exp(\pm i\pi P_{c,\rho}/4)$$

In the present exemplary embodiment, the quantum computer 120 measures the quantity expressed in the following equation based on the quantum circuit illustrated in FIG. 4.

$$\langle Q \mathbb{R} \rangle_{(a,\mu,\pm),(b,\nu,\pm),(c,\rho,\pm)}$$

Accordingly, the terms included in Equation (23) above are computable by quantum computation with the quantum computer 120, and the computation results thereof are measured.

$$-2\mathrm{Re}[\langle \phi_{(a,\mu),(b,\nu),(c,\rho)}(\theta^*(x))|Q|\psi(\theta^*(x))\rangle + \langle Q_{(a,\mu),(b,\nu)}$$
$$(\theta^*(x))|Q|\phi_{(c,\rho)}(\theta^*(x))\rangle + \langle Q_{(a,\mu),(c,\rho)}$$
$$(\theta^*(x))|Q|\phi_{(b,\nu)}(\theta^*(x))\rangle + (\phi_{(b,\nu),(c,\rho)}(\theta^*(x))|$$

$$Q|\phi_{(a,\mu)}(\nu^*(x))\rangle] = \langle Q \rangle_{(a,\mu,+),(b,\nu,+),(c,\rho,+)}^{-}$$
$$\langle Q \rangle_{(a,\mu,-),(b,\nu,-),(c,\rho,-)}^{-} + \langle Q \rangle_{(a,\mu,-),(b,\nu,-),(c,\rho,+)}^{+}$$
$$\langle Q \rangle_{(a,\mu,-),(b,\nu,+),(c,\rho,-)}^{-} + \langle Q \rangle_{(a,\mu,+),(b,\nu,-),(c,\rho,-)}^{-}$$
$$\langle Q \rangle_{(a,\mu,-),(b,\nu,+),(c,\rho,+)}^{-} - \langle Q \rangle_{(a,\mu,+),(b,\nu,-),(c,\rho,+)}^{-}$$
$$\langle Q \rangle_{(a,\mu,+),(b,\nu,+),(c,\rho,-)} \quad (24)$$

The third order partial derivative function of the energy E in Equation (23) above is thus obtainable based on the computation results of the quantum computation of Equation (24).

Other Partial Derivative Function Measurement

Next, explanation follows regarding computation of higher order partial derivative functions of the energy E. The derivative functions of energy E in Equation (25A) below are computable by similar procedures to the procedures described above.

$$\frac{\partial}{\partial \theta_a} \frac{\partial}{\partial \theta_b} \cdots \frac{\partial}{\partial \theta_c} \frac{\partial E}{\partial x_i} \quad (25A)$$

The derivative functions in Equation (25A) include derivative functions of energy E with respect to system-state-parameter x. Note that the derivative function of energy E with respect to parameter x may be computed by, for example, substituting the derivative function of the following equation for $h_Q$ in Equation (20) or Equation (23) above so as to compute the derivative function of Equation (25A). Note that the following equation corresponds to a derivative function of a Hamiltonian, and is thus computable with the classical computer 110.

$$\frac{\partial h_Q}{\partial x_i}$$

As another example, a derivative function such as that in Equation (25B) below appearing in Equation (8) above can also be computed using a similar procedure.

$$\frac{\partial}{\partial \theta_a} \frac{\partial}{\partial x_i} \frac{\partial E}{\partial x_k} \quad (25B)$$

Present Exemplary Embodiment Hybrid System 100: Summary of Operation

The hybrid system 100 of the present exemplary embodiment executes the various computation processing described above using the classical computer 110 and the quantum computer 120. More specifically, the hybrid system 100 computes derivative functions of energy E according to routines (A) to (F) below.

(A) The quantum computer 120 of the hybrid system 100 executes a VQE to obtain the optimal parameter θ* (x) for the quantum circuit U (θ).

(B) The classical computer 110 of the hybrid system 100 computes derivative functions of Hamiltonian H such as those of Equations (13) above.

(C) The classical computer 110 of the hybrid system 100 sets derivative functions of energy E for the system-state-parameter x according to Equation (6) to Equation (8) above.

(D) The quantum computer 120 of the hybrid system 100 finds the derivative functions of energy E with respect to parameter θ for the quantum circuit U (θ).

(E) The classical computer 110 of the hybrid system 100 finds the derivative function with respect to system-state-parameter x of the optimal parameter θ* for the quantum circuit U (θ), as expressed by the following equation, according to Equations (9), (10), and (11) above.

$$\frac{\partial \theta^*}{\partial x}$$

Note that the terms of the equations below that are present in Equations (9), (10), and (11) above are found at (D). Accordingly, the terms found at (D) for the equations below are substituted into Equations (9), (10), and (11) above to compute the derivative function of the parameter θ* for the quantum circuit U (θ) with respect to system-state-parameter x.

$$\frac{\partial}{\partial \theta_a} \frac{\partial E(\theta^*(x), x)}{\partial \theta_b}$$

$$\frac{\partial}{\partial \theta_a} \frac{\partial E(\theta^*(x), x)}{\partial x_i}$$

$$\frac{\partial}{\partial \theta_c} \frac{\partial}{\partial \theta_a} \frac{\partial E}{\partial \theta_b}$$

$$\frac{\partial}{\partial \theta_c} \frac{\partial}{\partial \theta_a} \frac{\partial E}{\partial x_j}$$

$$\frac{\partial}{\partial \theta_c} \frac{\partial}{\partial x_i} \frac{\partial E}{\partial x_j}$$

(F) The classical computer 110 of the hybrid system 100 substitutes the respective terms computed at (A) to (E) into Equations (6) to (8) above in order to obtain the derivative function of energy E with respect to system-state-parameter x.

First Exemplary Embodiment Hybrid System 100: Operation

Figure 5:
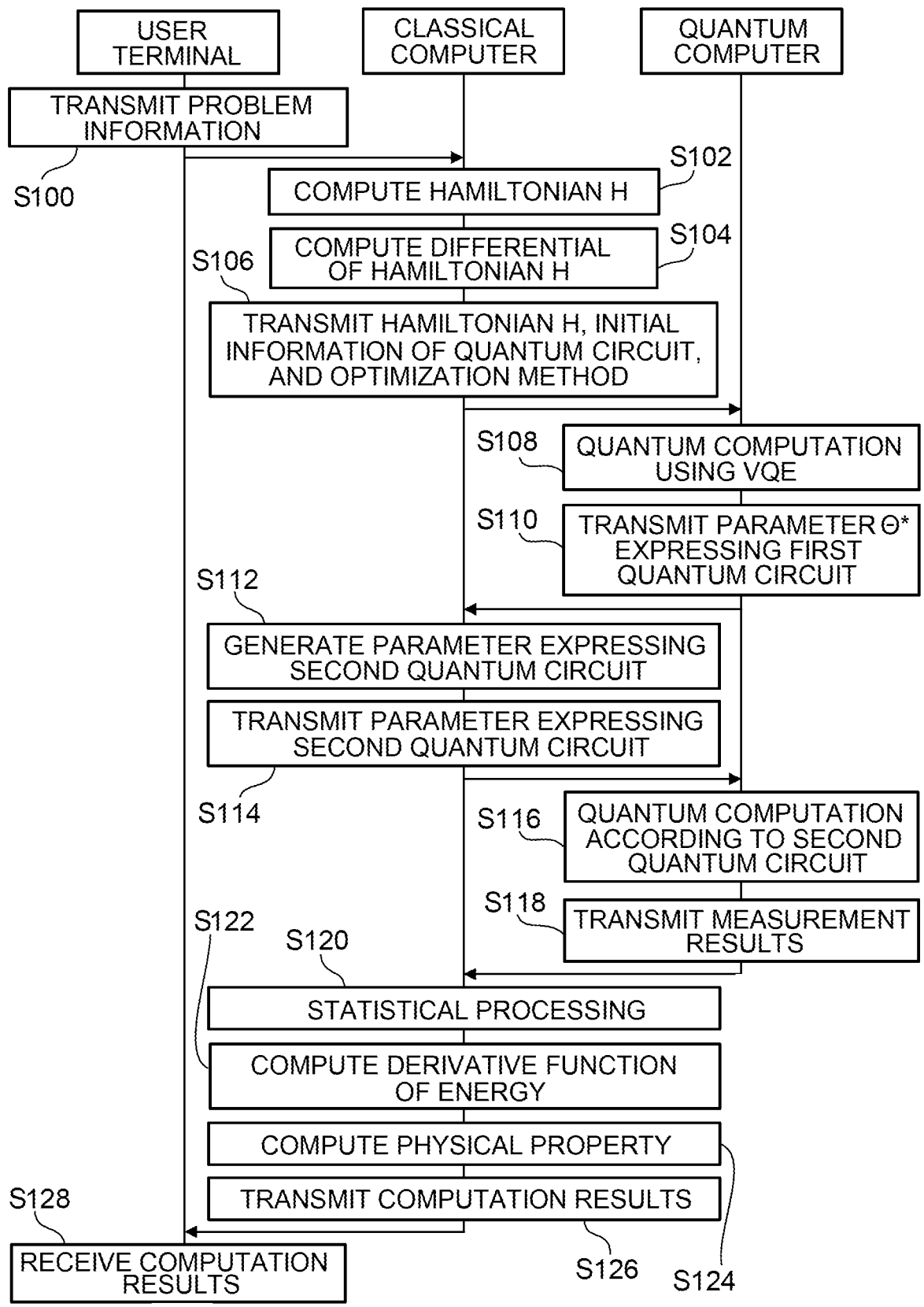
FIG. 5 is a diagram illustrating an example of computation processing for a derivative function of energy based on a parameter expressing a system state.

Next, explanation follows regarding specific operation of the hybrid system 100 of the first exemplary embodiment. The respective devices configuring the hybrid system 100 execute the various processing illustrated in FIG. 5.

First, at step S100, the user terminal 130 transmits problem information input by a user to the classical computer 110. The problem information is information relating to a problem to be solved by quantum computation, and this encompasses, for example, information relating to a substance to be analyzed and information relating to physical properties of this substance. Molecular parameters of the substance are an example of the information relating to the substance to be analyzed, and permittivity of a molecule to be analyzed is an example of the information relating to the physical properties.

Next, at step S102, the classical computer 110 receives the problem information transmitted from the user terminal 130. At step S102, based on information that relates to a molecule of a substance, from out of the received problem information, the classical computer 110 computes a Hamiltonian H expressing energy states of a system for the molecule according to Equation (12) above. Note that $h_P$ (x) in Equation (12) is set according to the information relating to the molecule of the substance to be analyzed.

At step S104, the classical computer 110 computes differentials of the Hamiltonian H based on the Hamiltonian H computed at step S102. Specifically, the classical computer 110 uses existing library software of quantum chemistry calculations to compute differentials of Equations (13) for the Hamiltonian H.

At step S106, the classical computer 110 outputs the Hamiltonian H computed at step S102 and initial information for the parameter $\theta$ expressing a quantum circuit. Specifically, the Hamiltonian H computed at step S102, the initial information for the parameter $\theta$ expressing the quantum circuit U ($\theta$), and an optimization method are transmitted to the quantum computer 120. The Nelder-Mead method is an example of the optimization method.

The data transmitted from the classical computer 110 to the quantum computer 120 at step S106 has a data structure employed in quantum computations by a quantum computer, and includes a Hamiltonian and initial information for parameters expressing a quantum circuit. This data structure is employed in processing to generate parameters of a first quantum circuit for computing the energy of a ground state or an excited state by quantum computation employing a VQE based on the Hamiltonian and the initial information.

At step S108, the control device 121 receives the Hamiltonian H, the initial information, and the optimization method that were transmitted from the classical computer at step S106. The control device 121 then causes the quantum computer 120 to execute the quantum computation employing the VQE according to the Hamiltonian H, the initial information, and the optimization method.

Specifically, under control by the control device 121, the quantum computer 120 generates an electromagnetic wave for irradiating at least one qubit out of the qubit cluster 123. The quantum computer 120 then subjects the at least one qubit out of the qubit cluster 123 to irradiation by the generated electromagnetic wave so as to execute a quantum circuit according to the initial information. The parameter $\theta^*$ expressing the first quantum circuit, this being an optimal quantum circuit, is accordingly generated thereby. Gate operations of quantum gates in the quantum circuit are converted into corresponding electromagnetic waveforms, and the qubit cluster 123 is irradiated by the electromagnetic wave generation device 122 with the generated electromagnetic waves. The quantum computer 120 then outputs the parameter $\theta^*$ expressing the first quantum circuit.

At step S110, the control device 121 transmits the parameter $\theta^*$ expressing the first quantum circuit obtained at step S108 to the classical computer 110.

At step S112, the classical computer 110 receives the parameter $\theta^*$ expressing the first quantum circuit as transmitted from the control device 121 at step S110. The classical computer 110 then generates parameters expressing a second quantum circuit including rotation gates according to the parameter $\theta^*$ expressing the first quantum circuit.

Specifically, the classical computer 110 generates a second quantum circuit such as that illustrated in FIG. 3 and FIG. 4 according to the parameter $\theta^*$ expressing the first quantum circuit. The second quantum circuit is a quantum circuit in which the rotation gates of Equation (21) above are inserted between plural unitary gates included in the first quantum circuit corresponding to the optimal parameter $\theta^*$.

The second quantum circuit for computing the derivative function of energy E is generated by inserting the rotation gates between the plural unitary gates in the first quantum circuit. The quantum computer 120 executes the second quantum circuit to compute the quantities expressed by Equation (22) and Equation (24) above.

At step S114, the classical computer 110 transmits parameters expressing the second quantum circuit generated at step S112 to the quantum computer 120.

The data transmitted from the classical computer 110 to the quantum computer 120 at step S114 has a data structure relating to the configuration of a quantum circuit employed in quantum computation by the quantum computer 120, and includes plural unitary gates, and the rotation gates inserted between the plural unitary gates. This data structure is employed in processing to measure quantum computation measurement results from quantum computation based on the quantum circuit including the plural unitary gates and rotation gates.

At step S116, the control device 121 receives the parameters expressing the second quantum circuit transmitted from the classical computer at step S114. The control device 121 then causes the quantum computer 120 to execute quantum computation according to the second quantum circuit. The quantum computer 120 thus executes quantum computation according to the parameters expressing the second quantum circuit.

Specifically, in response to control by the control device 121, the quantum computer 120 generates electromagnetic waves for irradiating at least one qubit out of the qubit cluster 123. The quantum computer 120 then subjects the at least one qubit out of the qubit cluster 123 to irradiation with the generated electromagnetic waves so as to execute the second quantum circuit and to thereby measure observed information. The quantum computer 120 then outputs the measurement results obtained by the quantum computation.

For example, bit strings such as those in the table below may be obtained as measurement results. The table below lifts sample counts obtained when a given quantum circuit is executed. The table below illustrates an example in which, when the quantum circuit is executed, a sample count of "10" is obtained for "0000", a sample count of "50" is obtained for "0001", a sample count of "14" is obtained for "0010", a sample count of "12" is obtained for "0011", and a sample count of "85" is obtained for "0100".

TABLE 1

| | Sample Count |
|---|---|
| 0000 | 10 |
| 0001 | 50 |
| 0010 | 14 |
| 0011 | 12 |
| 0100 | 85 |
| . | . |
| . | . |
| . | . |

At step S118, the control device 121 transmits the measurement results obtained at step S116 to the classical computer 110.

At step S120, the classical computer 110 receives the measurement results transmitted from the control device 121 at step S118. The classical computer 110 then performs statistical processing on the measurement results to calculate the second order partial derivative function of energy E with respect to parameter θ as in Equation (20) above and the third order partial derivative function of the energy E with respect to parameter θ as in Equation (23) above. Specifically, the classical computer 110 performs statistical processing on the obtained bit strings to compute expected values of the partial derivative functions. The classical computer 110 then employs the technology disclosed in Reference Document 1 to compute the first order partial derivative function of energy E with respect to parameter θ. The classical computer 110 also computes derivative functions such as those in Equation (25A) and Equation (25B) above.

At step S122, the classical computer 110 computes derivative functions of energy E corresponding to the Hamiltonian H, with respect to system-state-parameter x, according to the derivative functions of Hamiltonian H computed at step S104 and the respective derivative functions of energy E with respect to parameter θ obtained at step S120 in accordance with the quantum computation measurement results.

Specifically, at step S122, the classical computer 110 substitutes the Hamiltonian H computed at step S102, the derivative functions of the Hamiltonian H computed at step S104, and the respective derivative functions computed at step S120 into Equation (6), Equation (7), and Equation (8) to compute respective derivative functions of energy E with respect to system-state-parameter x.

At step S124, the classical computer 110 computes physical properties for the problem information received at step S102 based on the respective derivative functions of energy E with respect to system-state-parameter x obtained at step S122. Physical properties of a molecular of the substance are thus obtained for the problem information transmitted by the user terminal 130.

At step S126, the classical computer 110 transmits the computation results of the physical properties obtained at step S124 to the user terminal 130.

At step S128, the user terminal 130 receives from the classical computer 110 the transmitted computation results of the physical properties obtained at step S124.

As described above, in the hybrid system of the first exemplary embodiment, the classical computer outputs a Hamiltonian H and initial information for parameters expressing a quantum circuit. The quantum computer then, based on the Hamiltonian and the initial information output by the classical computer, executes quantum computation employing a VQE to generate parameters expressing the first quantum circuit for computing the energy of a ground state, and outputs the parameters expressing the first quantum circuit. The classical computer then, based on the parameters expressing the first quantum circuit output from the quantum computer, generates parameters to express the second quantum circuit including rotation gates, and outputs the parameters expressing the second quantum circuit. The quantum computer then executes quantum computation according to the parameters expressing the second quantum circuit output from the classical computer, and outputs measurement results of the quantum computation. The classical computer then computes derivative functions of the energy for the Hamiltonian based on the measurement results output from the quantum computer and on the derivative functions of the Hamiltonian, and outputs these derivative functions of energy. This enables the derivative functions of energy to be obtained for quantum computation of the energy of a system by employing a VQE.

The derivative functions of energy E with respect to system-state-parameter x can accordingly be efficiently obtained by quantum computation of the energy of a system while employing a VQE by adopting this appropriate division of tasks between the classical computer and the quantum computer.

More specifically, the classical computer computes the Hamiltonian H and the derivative functions of Hamiltonian H, and the quantum computer quantum computes the derivative functions of energy E based on the VQE and the quantum circuit parameter θ. This enables the derivative functions of energy E with respect to system-state-parameter x to be efficiently obtained.

Moreover, as illustrated in FIG. 3 and FIG. 4, in the present exemplary embodiment, shallow quantum circuits are employed to compute the derivative functions of energy E with respect to system-state-parameter x. Such shallow quantum circuits are useful when employing a noisy intermediate-scale quantum computer (NISQ) device. The present exemplary embodiment thus enables the derivative functions of energy E with respect to system-state-parameter x to be efficiently obtained while suppressing errors of quantum computation.

Second Exemplary Embodiment Hybrid System 100

Next, explanation follows regarding a second exemplary embodiment. Since configuration of a hybrid system according to the second exemplary embodiment is similar to the configuration of the first exemplary embodiment, the same reference numerals are appended thereto and explanation thereof is omitted.

The hybrid system 100 of the second exemplary embodiment computes derivative functions of energy for excited states.

Methods of computing the energy of excited states by employing a VQE are disclosed in Reference Documents 3 to 6 below.

Reference Document 3: "Subspace-search Variational Quantum Eigensolver for Excited States" by K. M. Nakanishi, K. Mitarai, and K. Fujii at arXiv:1810.09434 (2018)

Reference Document 4: "Variational Quantum Algorithms for Discovering Hamiltonian Spectra" by S. Endo, T. Jones, S. McArdle, X. Yuan, and S. Benjamin at arXiv: 1806.05707 (2018)

Reference Document 5: "Variational Quantum Computation of Excited States" by O. Higgott, D. Wang, and S. Brierley at arXiv:1805.08138 (2018)

Reference Document 6: "Hybrid Quantum-Classical Hierarchy for Mitigation of Decoherence and Determination of Excited States" by J. R. McClean, M. E. Kimchi-Schwartz, J. Carter, and W. A. de Jong in Physical Review A 95, 042308 (2017)

In the second exemplary embodiment, explanation is given regarding an example in which the technology disclosed in Reference Document 4 or Reference Document 5 is employed to compute derivative functions of energy for excited states.

An $r^{th}$ excited state of a Hamiltonian $H_r$ (x) can be expressed by Equation (26) below, wherein $H_0$ (x) denotes a ground state of a given Hamiltonian. Note that Equation (26) assumes $\beta_s$ to be sufficiently large. Index r=1, 2, and so on represents the excited states.

$$H_r(x) := H_0(x) + \sum_{s=0}^{r-1} \beta_s |\psi^{(s)}(\theta^{(s)}(x))\rangle\langle\psi^{(s)}(\theta^{(s)}(x))|, \quad (26)$$

In Equation (26), the ground state is expressed by the following equation.

$$|\psi^{(0)}(\theta^{(0)}(x))\rangle \mathbb{R}$$

In the above equation, $\theta^{(0)}(x)$ represents an optimal parameter for the quantum circuit $U(\theta)$ in the ground state. In the first exemplary embodiment, the optimal parameter for the quantum circuit $U(\theta)$ in the ground state is expressed by $\theta^*(x)$, whereas in the second exemplary embodiment the optimal parameter for the quantum circuit $U(\theta)$ in the ground state is expressed by $\theta^{(0)}(x)$. Moreover, in the second exemplary embodiment, the following equation is established. Note that in the following equation, $U^{(r)}(\theta)$ has a similar structure to $U(\theta)$ of the first exemplary embodiment.

$$|\psi^{(r)}(\theta)\rangle \mathbb{R} = U^{(r)}(\theta)|0\rangle \mathbb{R}$$

The quantum computer 120 of the hybrid system 100 of the second exemplary embodiment is required to compute the internal product of two quantum states. The quantum computer 120 of the second exemplary embodiment is thus a quantum computer capable of computing the internal product of two quantum states.

An expected value for a state $|\psi^{(r)}(\theta)\rangle$ of the Hamiltonian $H_r(x)$ is expressed by the following equation.

$$E_r(\theta,x) = \langle\omega^{(r)}(\theta)|H_r(x)|\psi^{(r)}(\theta)\rangle \mathbb{R}.$$

An optimum energy for the $r^{th}$ excited state is defined by the following equation.

$$E_r^*(x) = E_r(\theta^{(r)}(x),x).$$

The hybrid system 100 of the second exemplary embodiment computes derivative functions of energy E* for an excited state with respect to system-state-parameter x. Note that for a Hamiltonian $H_r$ of the $r^{th}$ excited state, the energy $E_r^*$ of the $r^{th}$ excited state corresponds to a ground state energy. Accordingly, Equations (6), (7), and (8) are also applicable to computing derivative functions of the excited state energy E*.

Equation (6) above corresponds to a first order partial derivative function of the energy E of the $r^{th}$ excited state with respect to system-state-parameter x. Equation (7) above corresponds to a second order partial derivative function of the energy E of the $r^{th}$ excited state with respect to system-state-parameter x. The first order partial derivative function of the energy E of the $r^{th}$ excited state and the second order partial derivative function of the energy E of the $r^{th}$ excited state can be expressed by the equations below.

$$\frac{\partial E_r^*}{\partial x_i}$$

$$\frac{\partial^2 E_r^*}{\partial x_i \partial x_j}$$

However, the classical computer 110 is not able to compute the derivative functions of Hamiltonian $H_r$ for an excited state. The derivative function of the Hamiltonian $H_r$ for an excited state can be expressed by Equation (27) below.

$$\frac{\partial H_r}{\partial x_i}(x) = \frac{\partial H_0}{\partial x_i}(x) + \sum_{s=0}^{r-1} \beta_s \left(\frac{\partial|\psi^{(s)}(\theta^{(s)}(x))\rangle}{\partial x_i}\langle\psi^{(s)}(\theta^{(s)}(x))| + h.c.\right) \quad (27)$$

$$= \frac{\partial H_0}{\partial x_i}(x) +$$

$$\sum_{s=0}^{r-1}\sum_a \beta_s \frac{\partial \theta_a^{(s)}}{\partial x_i}(x)\left(|\partial_a\psi^{(s)}(\theta^{(s)}(x))\rangle\langle\psi^{(s)}(\theta^{(s)}(x))| + h.c.\right).$$

Substituting Equation (27) into Equation (6) above results in the following equation. The quantum computer 120 of the hybrid system 100 of the second exemplary embodiment performs quantum computation of the following equation.

$$\text{Re}[\langle \psi^{(r)}(\theta^{(r)}(x))|\partial_a\psi^{(s)}(\theta^{(s)}(x))\rangle\langle \mathbb{R} \psi^{(s)}(\theta^{(s)}(x))|\psi^{(r)}(\theta^{(r)}(x))\rangle \mathbb{R}].$$

Internal Product Measurement

The internal product of quantum states, as in the following equation, can be expanded so as to expressed in the format shown by Equation (28) below.

$$\text{Re}[\langle\psi^{(r)}(\theta^{(r)}(x))|\partial_a\psi^{(s)}(\theta^{(s)}(x))\rangle\langle\psi^{(s)}(\theta^{(s)}(x))|\psi^{(r)}(\theta^{(r)}(x))\rangle]. \quad (28)$$

$$\text{Re}[\langle\psi^{(r)}(\theta^{(r)}(x))|\partial_a\psi^{(s)}(\theta^{(s)}(x))\rangle\langle\psi^{(s)}(\theta^{(s)}(x))|\psi^{(r)}(\theta^{(r)}(x))\rangle] =$$

$$\sum_\mu g_{a,\mu}^{(s)}\text{Re}[\langle\psi^{(r)}(\theta^{(r)}(x))|\phi_{(a,\mu)}^{(s)}(\theta^{(s)}(x))\rangle\langle\psi^{(s)}(\theta^{(s)}(x))|\psi^{(r)}(\theta^{(r)}(x))\rangle].$$

$\phi^{(s)}_{(a,\mu)}$ in Equation (28) follows Equation (19) above. Each of the terms inside $\Sigma$ in Equation (28) is computed using the following relationship equation.

$$\left|\langle\psi^{(r)}(\theta^{(r)}(x))|\left(\frac{1}{\sqrt{2}}(|\psi^{(s)}(\theta^{(s)}(x))\rangle + |\phi_{(a,\mu)}^{(s)}(\theta^{(s)}(x))\rangle)\right)\right|^2 = \quad (29)$$

$$\frac{1}{2}(|\langle\psi^{(r)}(\theta^{(r)}(x))|\psi^{(s)}(\theta^{(s)}(x))\rangle|^2 + |\langle\psi^{(r)}(\theta^{(r)}(x))|\phi_{(a,\mu)}^{(s)}(\theta^{(s)}(x))\rangle|^2 +$$

$$2\text{Re}[\langle\psi^{(r)}(\theta^{(r)}(x))|\phi_{(a,\mu)}^{(s)}(\theta^{(s)}(x))\rangle\langle\psi^{(s)}(\theta^{(s)}(x))|\psi^{(r)}(\theta^{(r)}(x))\rangle])$$

The quantum computer 120 of the second exemplary embodiment performs quantum computation of the left side of Equation (29) and of the first term and the second term on the right side of Equation (29). The classical computer 110 of the second exemplary embodiment computes the third term on the right side of Equation (29) based on the computation results of quantum computation for the left side of Equation (29) and for the first term and the second term on the right side of Equation (29).

Note that the quantum state of the following equation needs to be computed in order to compute the left side of Equation (29).

$$\frac{1}{\sqrt{2}}(|\psi^{(s)}(\theta^{(s)}(x))\rangle + |\phi^{(s)}_{(a,\mu)}(\theta^{(s)}(x))\rangle)$$

The quantum state expressed by the above equation may be easily generated by the quantum circuit as expressed by Equation (30A) below.

$$\frac{1}{\sqrt{2}}(|\psi^{(s)}(\theta^{(s)}(x))\rangle + |\phi^{(s)}_{(a,\mu)}(\theta^{(s)}(x))\rangle) = \quad (30A)$$
$$U^{(s)}_{N_s}(\theta^{(s)}_{N_s}(x)) \ldots U^{(s)}_a(\theta^{(s)}_a(x))R^{(s),+}_{a,\mu}U^{(s)}_{a-1}(\theta^{(s)}_{a-1}(x)) \ldots U^{(s)}_1(\theta^{(s)}_1(x))|0\rangle,$$

Equation (30A) corresponds to, for example, inserting rotation gates between plural unitary gates. For example, the rotation gate $R^{(s),+}_{a,\mu}$ in the following equation is inserted between an $a^{th}$ unitary gate and an $a-1^{th}$ unitary gate.

$$R_{a,\mu}^{(s),+}=\exp(i\pi P_{a,\mu}^{(s)}/4)$$

$$P_{a,\mu}^{(s)} \in \mathcal{P}. \quad (30B)$$

The quantum computer 120 executes the quantum circuit having the rotation gates inserted between the plural unitary gates so as to measure the right side of Equation (29) above.

The above method may be extended to other terms. For example, expanding Equation (31) below, which corresponds to Equation (6), produces a term such as that of Equation (32) below.

$$\text{Re}\left[\langle\psi^{(r)}(\theta^{(r)}(x))|\frac{\partial H_r}{\partial x_i}(x)|\partial_b\psi^{(r)}(\theta^{(r)}(x))\rangle\right]. \quad (31)$$

$$\text{Re}[\langle\psi^{(r)}(\theta^{(r)}(x))|\partial_a\psi^{(s)}(\theta^{(s)}(x))\rangle\langle\psi^{(s)}(\theta^{(s)}(x))|\partial_b\psi^{(r)}(\theta^{(r)}(x))\rangle + \quad (32)$$
$$\langle\psi^{(r)}(\theta^{(r)}(x))|\psi^{(s)}(\theta^{(s)}(x))\rangle\langle\partial_a\psi^{(s)}(\theta^{(s)}(x))|\partial_b\psi^{(r)}(\theta^{(r)}(x))\rangle].$$

Equation (33) below is employed when performing the quantum computation of Equation (32).

$$\text{Re}[\langle\psi^{(r)}(\theta^{(r)}(x))|\phi^{(s)}_{(a,\mu)}(\theta^{(s)}(x))\rangle\langle\psi^{(s)}(\theta^{(s)}(x))|\phi^{(r)}_{(b,\nu)}(\theta^{(r)}(x))\rangle + \quad (33)$$
$$\langle\psi^{(r)}(\theta^{(r)}(x))|\psi^{(s)}(\theta^{(s)}(x))\rangle\langle\phi^{(s)}_{(a,\mu)}(\theta^{(s)}(x))|\phi^{(r)}_{(b,\nu)}(\theta^{(r)}(x))\rangle] =$$
$$\left|\frac{1}{\sqrt{2}}(\langle\psi^{(s)}(\theta^{(s)}(x))| + \langle\phi^{(s)}_{(a,\mu)}(\theta^{(s)}(x))|)\frac{1}{\sqrt{2}}(|\psi^{(r)}(\theta^{(r)}(x))\rangle + |\phi^{(r)}_{(b,\nu)}(\theta^{(r)}(x))\rangle)\right|^2 +$$
$$\left|\frac{1}{\sqrt{2}}(\langle\psi^{(s)}(\theta^{(s)}(x))| - \langle\phi^{(s)}_{(a,\mu)}(\theta^{(s)}(x))|)\frac{1}{\sqrt{2}}(|\psi^{(r)}(\theta^{(r)}(x))\rangle - |\phi^{(r)}_{(b,\nu)}(\theta^{(r)}(x))\rangle)\right|^2 -$$
$$\frac{1}{2}(|\langle\psi^{(s)}(\theta^{(s)}(x))|\psi^{(r)}(\theta^{(r)}(x))\rangle|^2 + |\langle\phi^{(s)}_{(a,\mu)}(\theta^{(s)}(x))|\psi^{(r)}(\theta^{(r)}(x))\rangle|^2 +$$
$$|\langle\psi^{(s)}(\theta^{(s)}(x))|\phi^{(r)}_{(b,\nu)}(\theta^{(r)}(s))\rangle|^2 + |\langle\phi^{(s)}_{(a,\mu)}(\theta^{(s)}(x))|\phi^{(r)}_{(b,\nu)}(\theta^{(r)}(x))\rangle|^2)$$

Equation (32) can be computed by using the quantum computer 120 to compute all of the terms on the right side of Equation (33).

In the second exemplary embodiment, the rotation gates $R^{(s),\pm}_{a,\mu}$ and $R^{(r),\pm}_{a,\mu}$ of the following equation are inserted between unitary gates to compute the quantum states of each of the above Equations.

$$R_{a,\mu}^{(s),\pm}=\exp(\pm i\pi P_{a,\mu}^{(s)}/4)$$

$$R_{a,\mu}^{(r),\pm}=\exp(\pm i\pi P_{a,\mu}^{(r)}/4)$$

Second Exemplary Embodiment Hybrid System 100: Operation

Next, explanation follows regarding operation of the hybrid system 100 of the second exemplary embodiment. Similarly to in the first exemplary embodiment, the respective devices configuring the hybrid system 100 of the second exemplary embodiment execute the respective processing illustrated in FIG. 5.

The processing of step S100 to step S110 is executed similarly to in the first exemplary embodiment.

At step S112, based on the parameter θ* expressing the first quantum circuit, the classical computer 110 of the second exemplary embodiment generates a parameter expressing the second quantum circuit including rotation gates.

Specifically, the classical computer 110 of the second exemplary embodiment generates the second quantum circuit by inserting the rotation gate expressed by Equation (30B) between the plural unitary gates included in the first quantum circuit corresponding to the optimal parameter θ*.

The processing of step S114 to step S126 is executed similarly to in the first exemplary embodiment.

As described above, the classical computer of the hybrid system of the second exemplary embodiment inserts rotation gates corresponding to excited states between the plural unitary gates included in the first quantum circuit so as to compute derivative functions of energy for excited states. This enables derivative functions of energy for excited states to be obtained when quantum computing the energy of a system employing a VQE.

Example 1

Next, explanation follows regarding an Example. In the present Example, numerical value simulation was performed using an electron Hamiltonian for a hydrogen molecule. In the present Example, the Hamiltonian is computed by employing existing open-source libraries PySCF (see Reference Document 7: Q. Sun, T. C. Berkelbach, N. S. Blunt, G. H. Booth, S. Guo, Z. Li, J. Liu, J. D. McClain, E. R. Sayfutyarova, S. Sharma, S. Wouters, and G. K. Chan, in Wiley Interdisciplinary Reviews: Computational Molecular Science 8, e1340 (2017)) and OpenFermion (see Reference Document 8: J. R. McClean, K. J. Sung, I. D. Kivlichan, Y. Cao, C. Dai, E. S. Fried, C. Gidney, B. Gimby, P. Gokhale, T. Hner, T. Hardikar, V. Havlek, O. Higgott, C. Huang, J. Izaac, Z. Jiang, X. Liu, S. McArdle, M. Neeley, T. O'Brien, B. O'Gorman, I. Ozdan, M. D. Radin, J. Romero, N. Rubin, N. P. D. Sawaya, K. Setia, S. Sim, D. S. Steiger, M. Steudtner, Q. Sun, W. Sun, D. Wang, F. Zhang, and R.

Babbush at arXiv:1710.07629 (2017)). Quantum circuit simulations were then carried out using Qulacs (see https://github.com/qulacs/qulacs).

Figure 6:
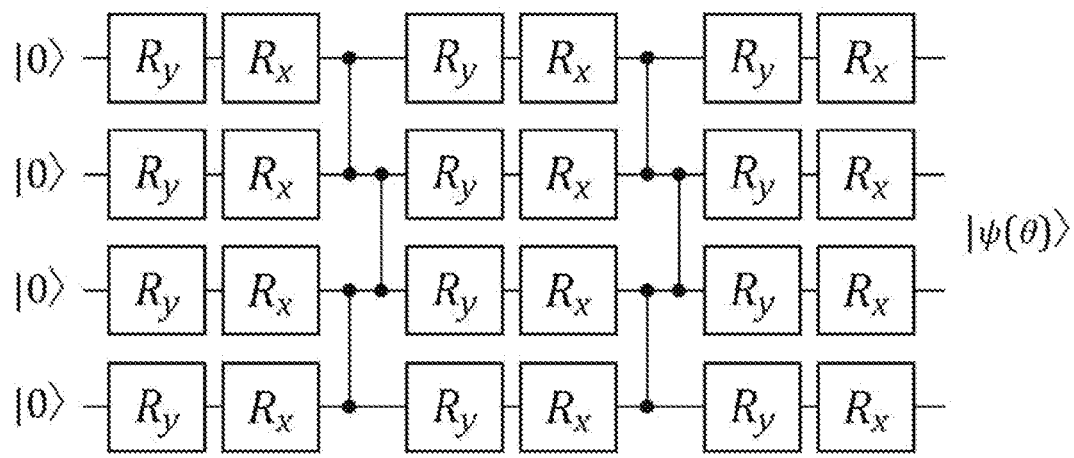
FIG. 6 is a diagram illustrating a hypothetical quantum circuit employed in a simulation.
Figure 7:
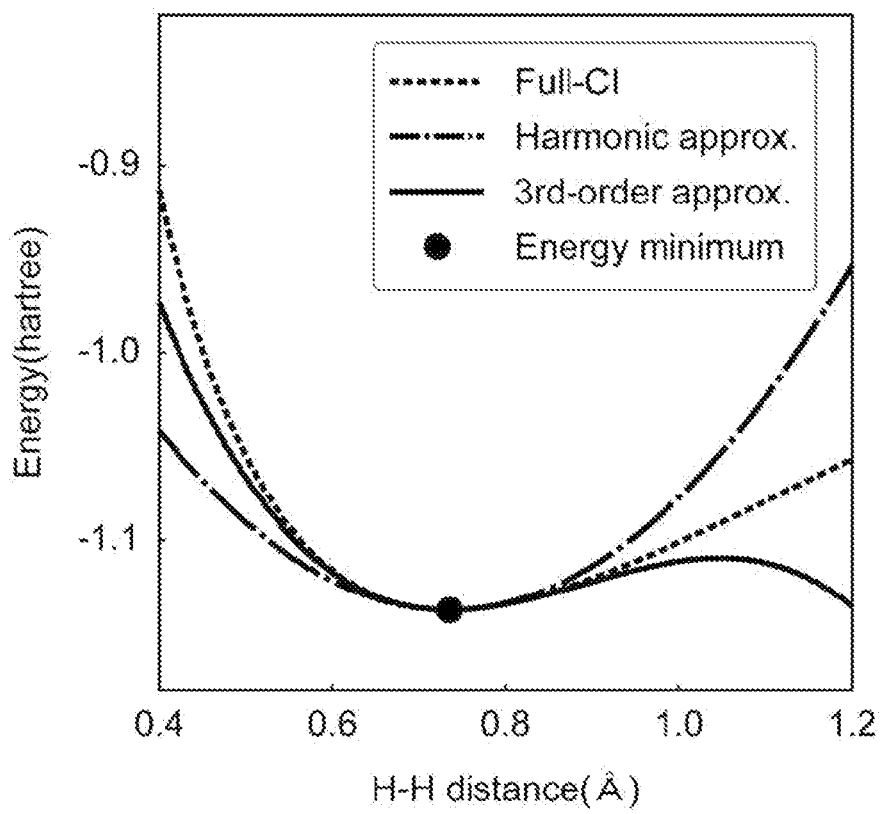
FIG. 7 is a diagram illustrating an example of simulation results.

FIG. 6 illustrates a quantum circuit employed in numerical value simulation. Ry and Rx respectively represent y-axis rotation gates and x-axis rotation gates. FIG. 7 illustrates a second order approximation curve and a third order approximation curve drawn for an energy curve to find the second order differential and third order differential for energy in a simulation using the quantum circuit of FIG. 6 and the Hamiltonian of a hydrogen molecule, for a numerical value simulation using the present method of the distance between hydrogen atoms as parameter x of the Hamiltonian. Note that in FIG. 7, "Full-CI" represents logical values, "Harmonic approx." represents the second order approximation curve, "3rd-order approx." represents the third order approximation curve, and "Energy minimum" represents a minimum of the energy. It can be seen in FIG. 7 that approximation curves can be found with good precision.

Note that the technology disclosed herein is not limited to the exemplary embodiments described above, and various modifications and applications are possible within arrange not departing from the spirit of the present disclosure.

For example, in the exemplary embodiments described above, information may be exchanged in any manner between the classical computer 110 and the quantum computer 120. For example, between the classical computer 110 and the quantum computer 120, the exchange of parameters expressing quantum circuits, the exchange of measurement results, and the like may be performed by successive exchanges performed each time a predetermined computation is completed, or may be performed by exchange after all computations have been completed.

Moreover, in the exemplary embodiments described above, explanation has been given regarding an example in which problem information is transmitted from the user terminal 130 to the classical computer 110, and the classical computer 110 computes the Hamiltonian H based on the problem information. However, there is no limitation thereto. For example, in cases in which a user operating the user terminal 130 is able to express the problem as a Hamiltonian, the classical computer 110 may receive the Hamiltonian H as the problem information. The user terminal 130 may transmit the problem information over a computer network such as an IP network to the classical computer 110 or to a storage medium or storage device accessible to the classical computer 110. Alternatively, the problem information may be stored on a storage medium or storage device and then passed to the administrator of the classical computer 110 for the administrator to input the problem information to the classical computer 110 using the storage medium or storage device.

In the respective exemplary embodiments described above, explanation has been given regarding examples in which the problem information includes information relating to a substance to be analyzed and information relating to physical properties of this substance, and physical properties are computed based on the derivative functions of energy E corresponding to the substance to be analyzed. However, there is no limitation thereto. For example, information relating to a predetermined optimization problem may be given as the problem information. In such cases, the hybrid system 100 computes the derivative functions of energy E with respect to the system-state-parameter x for the given optimization problem. For example, as an example of an optimization problem, when a traveling salesman problem is given as the problem information, a cost function of the total distance between locations to be visited is set as the energy function E, and the derivative functions of the cost function are computed with respect to parameter x representing the distance between the locations to be visited.

Moreover, in the respective exemplary embodiments described above, explanation has been given regarding examples of cases in which an angle of the rotation gates is $\pi/4$, as expressed by Equation (21) and Equation (30B) above. However, there is no limitation thereto, and any angle may be employed therefor. For example, $\pi/3$ may be employed as the angle of the rotation gates. For cases in which the angle of the rotation gates is modified, Equation (21) and Equation (30B) above should be appropriately modified to a format applicable to the angle of the rotation gates.

In the respective exemplary embodiments described above, explanation has been given regarding an example of a case in which the quantum circuits are executed by irradiating electromagnetic waves. However, there is no limitation thereto, and quantum circuits may be executed using a different method.

Although the respective exemplary embodiments described above assume that the classical computer 110 and the quantum computer 120 are administered by separate organizations, the classical computer 110 and the quantum computer 120 may be administered as one by the same organization. In such cases, there is no longer a need to transmit quantum computation information from the classical computer 110 to the quantum computer 120, or to transmit measurement results from the quantum computer 120 to the classical computer 110. Moreover, in such cases the role of the classical computer 110 in the foregoing explanation may conceivably be performed by the control device 121 of the quantum computer 120.

Note that in the foregoing respective exemplary embodiments described in the present specification, unless the word "solely" is used, as in "based solely on xx", "according solely to xx", or "solely in the case of xx", this should be deemed to mean that consideration of other additional information may also be anticipated. For example, wording such as "in the case of A, then B" should be deemed not to mean that "B is always be true in the case of A", unless clearly stated as such.

Moreover, even if there is an aspect in which an operation different to the operations described in the present specification is performed in a method, program, terminal, device, server, or system (hereafter "method or the like"), the aspects of the technology disclosed herein concern operations the same as operations described in the present specification, and the additional presence of the operation different to the operations described in the present specification does not cause the method or the like to fall outside the scope of the aspects of the technology disclosed herein.

Although explanation has been given regarding exemplary embodiments in which a program is pre-installed, such a program may be provided stored on a computer-readable recording medium.

The processing executed by the CPU reading software (a program) in the exemplary embodiments described above may be executed by various types of processor other than a CPU. Such processors include programmable logic devices (PLD) that allow circuit configuration to be modified post-manufacture, such as a field-programmable gate array (FPGA), and dedicated electric circuits, these being processors including a circuit configuration custom-designed to execute specific processing, such as an application specific integrated circuit (ASIC). The processing may be executed by any one of these various types of processor, or by a combination of two or more of the same type or different types of processor (such as plural FPGAs, or a combination of a CPU and an FPGA). The hardware structure of these various types of processors is more specifically an electric circuit combining circuit elements such as semiconductor elements.

Moreover, although in the exemplary embodiments described above explanation has been given regarding a mode in which a program is stored (installed) in advance in storage, there is no limitation thereto. A program may be provided in a format stored on a non-transitory storage medium such as compact disk read only memory (CD-ROM), digital versatile disk read only memory (DVD-ROM), or universal serial bus (USB) memory. Alternatively, a program may be configured in a format downloadable from an external device over a network.

The respective processing of the present exemplary embodiments may be performed by a configuration of a computer, server, or the like including a generic computation processing device and storage device, with the respective processing being executed by a program. Such a program may be stored in the storage device, provided recorded on a recording medium such as a magnetic disk, an optical disk, or semiconductor memory, or provided over a network. Obviously any other configuration elements are also not limited to implementation by a single computer or server, and they may be distributed between plural computers connected together over a network and implemented thereon.

For example, the processing executed by the classical computer in the respective exemplary embodiments described above may be distributed between and performed by plural classical computers connected over a network. Alternatively, for example, the processing executed by the quantum computer in the respective exemplary embodiments described above may be distributed between and performed by plural quantum computers connected over a network.

Although explanation has been given regarding an example of a case in which the quantum computer performs quantum computation in the respective exemplary embodiments described above, there is no limitation thereto. For example, quantum computations may be executed by a classical computer that simulates the behavior of a quantum computer.

The disclosure of Japanese Patent Application No. 2019-090332, filed on May 13, 2019, is incorporated in its entirety in the present specification by reference herein. All cited documents, patent applications, and technical standards mentioned in the present specification are incorporated by reference in the present specification to the same extent as if each individual cited document, patent application, or technical standard was specifically and individually indicated to be incorporated by reference.

In the case of related technology, for example, the VQE disclosed in Document 1 ("A Variational Eigenvalue Solver on a Photonic Quantum Processor" by A. Peruzzo, J. McClean, P. Shadbolt, M-H. Yung, X-Q. Zhou, P. J. Love, A. Aspuru-Guzik and J. L. O'Brien in Nature Communications 5 Article number 4213 (2014)) does not consider the derivation of the derivative functions for energy. Moreover, the technology disclosed in Document 2 ("Quantum Algorithm for Molecular Properties and Geometry Optimization" by I. Kassal and A. Aspuru-Guzik in Journal of Chemical Physics 131, 224102 (2009)) utilizes quantum phase estimation when calculating derivative functions of energy, and makes no disclosure regarding the calculation of derivative functions of energy when calculating energy using a VQE.

In consideration of the above circumstances, an object of technology disclosed herein is to provide a quantum information processing method for finding a differential of energy that is able to obtain a derivative function of energy when performing quantum computation of energy in a system by employing a VQE. The technology disclosed herein also provides a classical computer, a quantum computer, a hybrid system, a quantum information processing program, and a data structure of the same.

The technology disclosed herein is accordingly able to exhibit the advantageous effects of being able to obtain a derivative function of energy when performing quantum computation of energy of a system employing a VQE.

A first aspect of the present disclosure is a quantum information processing method for finding a differential of energy by processing executed on a hybrid system including a classical computer and a quantum computer. The quantum information processing method includes: the classical computer outputting a Hamiltonian and initial information of a parameter expressing a quantum circuit; the quantum computer, based on the Hamiltonian and the initial information output from the classical computer, executing quantum computation employing a Variational Quantum Eigensolver (VQE) to generate a parameter expressing a first quantum circuit for computing energy, and outputting the parameter expressing the first quantum circuit; the classical computer, based on the parameter expressing the first quantum circuit output from the quantum computer, generating a parameter expressing a second quantum circuit including a rotation gate, and outputting the parameter expressing the second quantum circuit; the quantum computer, based on the parameter expressing the second quantum circuit output from the classical computer, executing quantum computation and outputting measurement results of this quantum computation; and the classical computer, based on the measurement results output from the quantum computer, the Hamiltonian, and a derivative function of the Hamiltonian, computing a derivative function of energy corresponding to the Hamiltonian and outputting the derivative function of energy.

A second aspect of the present disclosure is a quantum information processing method for finding a differential of energy, wherein the Hamiltonian is a Hamiltonian of a substance.

A third aspect of the present disclosure is a quantum information processing method for finding a differential of energy, wherein the classical computer generates the parameter expressing the second quantum circuit by inserting the rotation gate between plural unitary gates in the first quantum circuit.

A fourth aspect of the present disclosure is a quantum information processing method for finding a differential of energy, wherein the classical computer inserts a rotation gate $R^{\pm}_{a,\mu}$ expressed by Equation (1) below between plural unitary gates in the first quantum circuit in order to compute the derivative function of energy for a ground state.

$$R_{a,\mu}{}^{\pm} = \exp(\pm i\pi P_{a,\mu}/4).$$

$$P_{a,\mu} \in \mathcal{P}.$$

$$\mathcal{P} = \{I, X, Y, Z\}^{\otimes n} \tag{1}$$

Wherein a is an index from among indices a, b, c, . . . used to discriminate between elements of a parameter vector θ of a quantum circuit, and μ is an index used to discriminate between Pauli operators.

A fifth aspect of the present disclosure is a quantum information processing method for finding a differential of energy, wherein the classical computer inserts a rotation gate $R^{(s),\pm}_{a,\mu}$ expressed by Equation (2) below between plural unitary gates in the first quantum circuit to compute the derivative function of energy for an excited state.

$$R_{a,\mu}^{(s),\pm} = \exp(i\pi P_{a,\mu}^{(s)}/4)$$

$$P_{a,\mu}^{(s)} \in \mathcal{P}.$$

$$\mathcal{P} = \{I,X,Y,Z\}^{\otimes n} \quad (2)$$

Wherein a is an index from among indices a, b, c, ... used to discriminate between elements of a parameter vector θ of a quantum circuit, μ is an index used to discriminate between Pauli operators, and s is an index to represent excited states.

A sixth aspect of the present disclosure is a quantum information processing method for finding a differential of energy, wherein the classical computer and the quantum computer are connected over a computer network, and the classical computer and the quantum computer exchange information with each other over the computer network.

A seventh aspect of the present disclosure is a quantum information processing method for finding a differential of energy by processing executed by a classical computer. The processing includes the classical computer: outputting a Hamiltonian and initial information of a parameter expressing a quantum circuit; according to a parameter expressing a first quantum circuit that was output from a quantum computer and was generated by quantum computation employing a Variational Quantum Eigensolver (VQE) based on the Hamiltonian and the initial information, generating a parameter expressing a second quantum circuit including a rotation gate and outputting the parameter expressing the second quantum circuit; and, based on measurement results of quantum computation that were output from the quantum computer and computed according to the parameter expressing the second quantum circuit, based on the Hamiltonian, and based on a derivative function of the Hamiltonian, generating a derivative function of energy corresponding to the Hamiltonian and outputting the derivative function of energy.

An eighth aspect of the present disclosure is a quantum information processing method for finding a differential of energy by processing executed by a quantum computer. The processing includes the quantum computer: based on a Hamiltonian and initial information of a parameter expressing a quantum circuit that were output from a classical computer, executing quantum computation employing a Variational Quantum Eigensolver (VQE) to generate a parameter expressing a first quantum circuit and outputting the parameter expressing the first quantum circuit; and based on a parameter that expresses a second quantum circuit including a rotation gate, that was output from a classical computer, and that accords with the parameter expressing the first quantum circuit, executing quantum computation and outputting measurement results of the quantum computation.

A ninth aspect of the present disclosure is a classical computer configured to execute processing. The processing includes: outputting a Hamiltonian and initial information of a parameter expressing a quantum circuit; according to a parameter expressing a first quantum circuit that was output from a quantum computer and was generated by quantum computation employing a Variational Quantum Eigensolver (VQE) based on the Hamiltonian and the initial information, generating a parameter expressing a second quantum circuit including a rotation gate and outputting the parameter expressing the second quantum circuit; and, based on measurement results of quantum computation that were output from the quantum computer and computed according to the parameter expressing the second quantum circuit, based on the Hamiltonian, and based on a derivative function of the Hamiltonian, generating a derivative function of energy corresponding to the Hamiltonian and outputting the derivative function of energy.

A tenth aspect of the present disclosure is a quantum computer configured to execute processing. The processing includes: based on a Hamiltonian and initial information of a parameter expressing a quantum circuit that were output from a classical computer, executing quantum computation employing a Variational Quantum Eigensolver (VQE) to generate a parameter expressing a first quantum circuit for computing energy and outputting the parameter expressing the first quantum circuit; and based on a parameter that expresses a second quantum circuit including a rotation gate, that was output from a classical computer, and that accords with the parameter expressing the first quantum circuit, executing quantum computation and outputting measurement results of the quantum computation.

An eleventh aspect of the present disclosure is a quantum information processing program to cause a classical computer to execute processing. The processing includes: outputting a Hamiltonian and initial information of a parameter expressing a quantum circuit; according to a parameter expressing a first quantum circuit for computing energy that was output from a quantum computer and was generated by quantum computation employing a Variational Quantum Eigensolver (VQE) based on the Hamiltonian and the initial information, generating a parameter expressing a second quantum circuit including a rotation gate and outputting the parameter expressing the second quantum circuit; and, based on measurement results of quantum computation that were output from the quantum computer and computed according to the parameter expressing the second quantum circuit, based on the Hamiltonian, and based on a derivative function of the Hamiltonian, generating a derivative function of energy corresponding to the Hamiltonian and outputting the derivative function of energy.

A twelfth aspect of the present disclosure is a quantum information processing program to cause a quantum computer to execute processing. The processing includes: based on a Hamiltonian and initial information of a parameter expressing a quantum circuit that were output from a classical computer, executing quantum computation employing a Variational Quantum Eigensolver (VQE) to generate a parameter expressing a first quantum circuit for computing energy and outputting the parameter expressing the first quantum circuit; and based on a parameter that expresses a second quantum circuit including a rotation gate, that was output from a classical computer, and that accords with the parameter expressing the first quantum circuit, executing quantum computation and outputting measurement results of the quantum computation.

A thirteenth aspect of the present disclosure is a data structure employed in quantum computation by a quantum computer. The data structure includes a Hamiltonian and initial information of a parameter expressing a quantum circuit. The data structure is employed in processing to generate a parameter of a first quantum circuit for computing energy of a ground state or of an excited state by quantum computation by the quantum computer employing a Variational Quantum Eigensolver (VQE) based on the Hamiltonian and the initial information.

A fourteenth aspect of the present disclosure is a data structure relating to configuration of a quantum circuit employed in quantum computation by a quantum computer. The data structure includes plural unitary gates and a rotation gate inserted between the plural unitary gates. The data structure is employed in processing to measure results of measurement by quantum computation performed by the quantum computer based on a quantum circuit including the plural unitary gates and the rotation gate.

A fifteenth aspect of the present disclosure is a hybrid system including the classical computer of the present disclosure and the quantum computer of the present disclosure.

What is claimed is:

1. A quantum information processing method for finding a differential of energy by processing executed on a hybrid system including a classical computer and a quantum computer, the quantum information processing method comprising:
the classical computer outputting a Hamiltonian and initial information of a parameter of a quantum circuit, wherein the Hamiltonian is a Hamiltonian of a substance;
the quantum computer, based on the Hamiltonian and the initial information output from the classical computer, executing quantum computation employing a method for computing an approximation of an eigenvalue for minimum of a Hamiltonian by variational updating of a parameter of a quantum circuit to generate a parameter of a first quantum circuit for computing energy, and outputting the parameter of the first quantum circuit;
the classical computer, based on the parameter of the first quantum circuit output from the quantum computer, generating a parameter of a second quantum circuit including a rotation gate by inserting the rotation gate between a plurality of unitary gates in the first quantum circuit, and outputting the parameter of the second quantum circuit;
the quantum computer, based on the parameter of the second quantum circuit output from the classical computer, executing quantum computation and outputting measurement results of this quantum computation; and
the classical computer, based on the measurement results output from the quantum computer, the Hamiltonian, and a derivative function of the Hamiltonian, computing a derivative function of energy corresponding to the Hamiltonian and outputting the derivative function of energy,
wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm}=\exp(\pm i\pi P_{a,\mu}/4)$$

$$P_{a,\mu}\in \mathcal{P}$$

$$\mathcal{P}=\{I,X,Y,Z\}^{\otimes n} \quad (1)$$

$$R_{a,\mu}^{(s),+}=\exp(i\pi P_{a,\mu}^{(s)}/4)$$

$$P_{a,\mu}^{(s)}\in \mathcal{P}$$

$$\mathcal{P}=\{I,X,Y,Z\}^{\otimes n} \quad (2)$$

wherein a is an index from among indices a, b, c, . . . used to discriminate between elements of a parameter vector of a quantum circuit, μ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

2. The quantum information processing method for finding a differential of energy of claim 1, wherein:
the classical computer and the quantum computer are connected over a computer network; and
the classical computer and the quantum computer exchange information with each other over the computer network.

3. A quantum information processing method for finding a differential of energy by processing executed by a classical computer, the processing comprising:
outputting a Hamiltonian and initial information of a parameter expressing of a quantum circuit;
according to a parameter of a first quantum circuit that was output from a quantum computer and was generated by quantum computation employing a method for computing an approximation of an eigenvalue for minimum of a Hamiltonian by variational updating of a parameter of a quantum circuit based on the Hamiltonian and the initial information, generating a parameter of a second quantum circuit including a rotation gate and outputting the parameter of the second quantum circuit; and
based on measurement results of quantum computation that were output from the quantum computer and computed according to the parameter of the second quantum circuit, based on the Hamiltonian, and based on a derivative function of the Hamiltonian, generating a derivative function of energy corresponding to the Hamiltonian and outputting the derivative function of energy,
wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm}=\exp(\pm i\pi P_{a,\mu}/4)$$

$$P_{a,\mu}\in \mathcal{P}$$

$$\mathcal{P}=\{I,X,Y,Z\}^{\otimes n} \quad (1)$$

$$R_{a,\mu}^{(s),+}=\exp(i\pi P_{a,\mu}^{(s)}/4)$$

$$P_{a,\mu}^{(s)}\in \mathcal{P}$$

$$\mathcal{P}=\{I,X,Y,Z\}^{\otimes n} \quad (2)$$

wherein a is an index from among indices a, b, c, . . . used to discriminate between elements of a parameter vector of a quantum circuit, μ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

4. A quantum information processing method for finding a differential of energy by processing executed by a quantum computer, the processing comprising:
- based on a Hamiltonian and initial information of a parameter of a quantum circuit that were output from a classical computer, executing quantum computation employing a method for computing an approximation of an eigenvalue for minimum of a Hamiltonian by variational updating of a parameter of a quantum circuit to generate a parameter of a first quantum circuit and outputting the parameter of the first quantum circuit;
- based on a parameter that expresses a second quantum circuit including a rotation gate, that was output from a classical computer, and that accords with the parameter of the first quantum circuit, executing quantum computation and outputting measurement results of the quantum computation; and
- based on measurement results of quantum computation, based on the Hamiltonian, and based on a derivative function of the Hamiltonian, generating a derivative function of energy corresponding to the Hamiltonian and outputting the derivative function of energy,
- wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm}=\exp(\pm i\pi P_{a,\mu}/4)$$

$$P_{a,\mu} \in \mathcal{P}$$

$$\mathcal{P}=\{I,X,Y,Z\}^{\otimes n} \tag{1}$$

$$R_{a,\mu}^{(s),+}=\exp(i\pi P_{a,\mu}^{(s)}/4)$$

$$P_{a,\mu}^{(s)} \in \mathcal{P}$$

$$\mathcal{P}=\{I,X,Y,Z\}^{\otimes n} \tag{2}$$

wherein a is an index from among indices a, b, c, ... used to discriminate between elements of a parameter vector of a quantum circuit, μ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

5. A classical computer configured to execute processing, the processing comprising:
- outputting a Hamiltonian and initial information of a parameter of a quantum circuit;
- according to a parameter of a first quantum circuit that was output from a quantum computer and was generated by quantum computation employing a method for computing an approximation of an eigenvalue for minimum of a Hamiltonian by variational updating of a parameter of a quantum circuit based on the Hamiltonian and the initial information, generating a parameter of a second quantum circuit including a rotation gate and outputting the parameter of the second quantum circuit; and
- based on measurement results of quantum computation that were output from the quantum computer and computed according to the parameter of the second quantum circuit, based on the Hamiltonian, and based on a derivative function of the Hamiltonian, generating a derivative function of energy corresponding to the Hamiltonian and outputting the derivative function of energy,
- wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm}=\exp(\pm i\pi P_{a,\mu}/4)$$

$$P_{a,\mu} \in \mathcal{P}$$

$$\mathcal{P}=\{I,X,Y,Z\}^{\otimes n} \tag{1}$$

$$R_{a,\mu}^{(s),+}=\exp(i\pi P_{a,\mu}^{(s)}/4)$$

$$P_{a,\mu}^{(s)} \in \mathcal{P}$$

$$\mathcal{P}=\{I,X,Y,Z\}^{\otimes n} \tag{2}$$

wherein a is an index from among indices a, b, c, ... used to discriminate between elements of a parameter vector of a quantum circuit, μ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

6. A quantum computer configured to execute processing, the processing comprising:
- based on a Hamiltonian and initial information of a parameter of a quantum circuit that were output from a classical computer, executing quantum computation employing a method for computing an approximation of an eigenvalue for minimum of a Hamiltonian by variational updating of a parameter of a quantum circuit to generate a parameter of a first quantum circuit for computing energy and outputting the parameter of the first quantum circuit;
- based on a parameter that expresses a second quantum circuit including a rotation gate, that was output from a classical computer, and that accords with the parameter of the first quantum circuit, executing quantum computation and outputting measurement results of the quantum computation; and
- based on measurement results of quantum computation, based on the Hamiltonian, and based on a derivative function of the Hamiltonian, generating a derivative function of energy corresponding to the Hamiltonian and outputting the derivative function of energy,
- wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm}=\exp(\pm i\pi P_{a,\mu}/4)$$

$$P_{a,\mu} \in \mathcal{P}$$

$$\mathcal{P}=\{I,X,Y,Z\}^{\otimes n} \tag{1}$$

$$R_{a,\mu}^{(s),+}=\exp(i\pi P_{a,\mu}^{(s)}/4)$$

$$P_{a,\mu}^{(s)}\in \mathcal{P}$$

$$\mathcal{P}=\{I,X,Y,Z\}^{\otimes n} \quad (2)$$

wherein a is an index from among indices a, b, c, . . . used to discriminate between elements of a parameter vector of a quantum circuit, μ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

7. A non-transitory recording medium storing a quantum information processing program to cause a classical computer to execute processing, the processing comprising:
outputting a Hamiltonian and initial information of a parameter of a quantum circuit;
according to a parameter of a first quantum circuit for computing energy that was output from a quantum computer and was generated by quantum computation employing a method for computing an approximation of an eigenvalue for minimum of a Hamiltonian by variational updating of a parameter of a quantum circuit based on the Hamiltonian and the initial information, generating a parameter of a second quantum circuit including a rotation gate and outputting the parameter of the second quantum circuit; and
based on measurement results of quantum computation that were output from the quantum computer and computed according to the parameter of the second quantum circuit, based on the Hamiltonian, and based on a derivative function of the Hamiltonian, generating a derivative function of energy corresponding to the Hamiltonian and outputting the derivative function of energy,
wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm}=\exp(\pm i\pi P_{a,\mu}/4)$$

$$P_{a,\mu}\in \mathcal{P}$$

$$\mathcal{P}=\{I,X,Y,Z\}^{\otimes n} \quad (1)$$

$$R_{a,\mu}^{(s),+}=\exp(i\pi P_{a,\mu}^{(s)}/4)$$

$$P_{a,\mu}^{(s)}\in \mathcal{P}$$

$$\mathcal{P}=\{I,X,Y,Z\}^{\otimes n} \quad (2)$$

wherein a is an index from among indices a, b, c, . . . used to discriminate between elements of a parameter vector of a quantum circuit, μ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

8. A non-transitory recording medium storing a quantum information processing program to cause a quantum computer to execute processing, the processing comprising:
based on a Hamiltonian and initial information of a parameter of a quantum circuit that were output from a classical computer, executing quantum computation employing a method for computing an approximation of an eigenvalue for minimum of a Hamiltonian by variational updating of a parameter of a quantum circuit to generate a parameter of a first quantum circuit for computing energy and outputting the parameter of the first quantum circuit;
based on a parameter that expresses a second quantum circuit including a rotation gate, that was output from a classical computer, and that accords with the parameter of the first quantum circuit, executing quantum computation and outputting measurement results of the quantum computation; and
based on measurement results of quantum computation, based on the Hamiltonian, and based on a derivative function of the Hamiltonian, generating a derivative function of energy corresponding to the Hamiltonian and outputting the derivative function of energy,
wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm}=\exp(\pm i\pi P_{a,\mu}/4)$$

$$P_{a,\mu}\in \mathcal{P}$$

$$\mathcal{P}=\{I,X,Y,Z\}^{\otimes n} \quad (1)$$

$$R_{a,\mu}^{(s),+}=\exp(i\pi P_{a,\mu}^{(s)}/4)$$

$$P_{a,\mu}^{(s)}\in \mathcal{P}$$

$$\mathcal{P}=\{I,X,Y,Z\}^{\otimes n} \quad (2)$$

wherein a is an index from among indices a, b, c, . . . used to discriminate between elements of a parameter vector of a quantum circuit, μ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

9. A hybrid system comprising:
the classical computer of claim 5; and
the quantum computer configured to execute processing, the processing comprising:
based on a Hamiltonian and initial information of a parameter of a quantum circuit that were output from a classical computer, executing quantum computation employing a method for computing an approximation of an eigenvalue for minimum of a Hamiltonian by variational updating of a parameter of a quantum circuit to generate a parameter of a first quantum circuit for computing energy and outputting the parameter of the first quantum circuit;
based on a parameter that expresses a second quantum circuit including a rotation gate, that was output from a classical computer, and that accords with the parameter of the first quantum circuit, executing quantum computation and outputting measurement results of the quantum computation.

10. A quantum information processing method for finding a differential of energy by processing executed by a classical computer, the processing comprising:

according to a parameter of a first quantum circuit that was output from a quantum computer and was generated by quantum computation employing a method for computing an approximation of an eigenvalue for minimum of a Hamiltonian by variational updating of a parameter of a quantum circuit based on a Hamiltonian and initial information, generating a parameter of a second quantum circuit including a rotation gate and outputting the parameter of the second quantum circuit; and based on measurement results of quantum computation that were output from the quantum computer and computed according to the parameter of the second quantum circuit, based on the Hamiltonian, and based on a derivative function of the Hamiltonian, generating a derivative function of energy corresponding to the Hamiltonian and outputting the derivative function of energy, wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm} = \exp(\pm i\pi P_{a,\mu}/4)$$

$$P_{a,\mu} \in \mathcal{P}$$

$$\mathcal{P} = \{I, X, Y, Z\}^{\otimes n} \tag{1}$$

$$R_{a,\mu}^{(s),+} = \exp(i\pi P_{a,\mu}^{(s)}/4)$$

$$P_{a,\mu}^{(s)} \in \mathcal{P}$$

$$\mathcal{P} = \{I, X, Y, Z\}^{\otimes n} \tag{2}$$

wherein a is an index from among indices a, b, c, ... used to discriminate between elements of a parameter vector of a quantum circuit, μ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

11. A classical computer configured to execute processing, the processing comprising:

according to a parameter of a first quantum circuit that was output from a quantum computer and was generated by quantum computation employing a method for computing an approximation of an eigenvalue for minimum of a Hamiltonian by variational updating of a parameter of a quantum circuit on a Hamiltonian and initial information, generating a parameter of a second quantum circuit including a rotation gate and outputting the parameter of the second quantum circuit; and based on measurement results of quantum computation that were output from the quantum computer and computed according to the parameter of the second quantum circuit, based on the Hamiltonian, and based on a derivative function of the Hamiltonian, generating a derivative function of energy corresponding to the Hamiltonian and outputting the derivative function of energy, wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm} = \exp(\pm i\pi P_{a,\mu}/4)$$

$$P_{a,\mu} \in \mathcal{P}$$

$$\mathcal{P} = \{I, X, Y, Z\}^{\otimes n} \tag{1}$$

$$R_{a,\mu}^{(s),+} = \exp(i\pi P_{a,\mu}^{(s)}/4)$$

$$P_{a,\mu}^{(s)} \in \mathcal{P}$$

$$\mathcal{P} = \{I, X, Y, Z\}^{\otimes n} \tag{2}$$

wherein a is an index from among indices a, b, c, ... used to discriminate between elements of a parameter vector of a quantum circuit, μ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

12. A non-transitory recording medium storing a quantum information processing program to cause a classical computer to execute processing, the processing comprising:

according to a parameter of a first quantum circuit for computing energy that was output from a quantum computer and was generated by quantum computation employing a method for computing an approximation of an eigenvalue for minimum of a Hamiltonian by variational updating of a parameter of a quantum circuit based on a Hamiltonian and initial information, generating a parameter of a second quantum circuit including a rotation gate and outputting the parameter of the second quantum circuit; and based on measurement results of quantum computation that were output from the quantum computer and computed according to the parameter of the second quantum circuit, based on the Hamiltonian, and based on a derivative function of the Hamiltonian, generating a derivative function of energy corresponding to the Hamiltonian and outputting the derivative function of energy, wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm} = \exp(\pm i\pi P_{a,\mu}/4)$$

$$P_{a,\mu} \in \mathcal{P}$$

$$\mathcal{P} = \{I, X, Y, Z\}^{\otimes n} \tag{1}$$

$$R_{a,\mu}^{(s),+} = \exp(i\pi P_{a,\mu}^{(s)}/4)$$

$$P_{a,\mu}^{(s)} \in \mathcal{P}$$

$$\mathcal{P} = \{I, X, Y, Z\}^{\otimes n} \tag{2}$$

wherein a is an index from among indices a, b, c, ... used to discriminate between elements of a parameter vector of a quantum circuit, µ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

13. A quantum information processing method for finding a differential of energy by processing executed on a hybrid system including at least one or more classical computers and at least one or more quantum computers, the quantum information processing method comprising:

a classical computer outputting a Hamiltonian and initial information of a parameter of a quantum circuit;

a quantum computer, based on the Hamiltonian and the initial information output from a classical computer, executing quantum computation employing a method for computing an approximation of an eigenvalue for minimum of a Hamiltonian by variational updating of a parameter of a quantum circuit to generate a parameter of a first quantum circuit for computing energy, and outputting the parameter of the first quantum circuit;

a classical computer, based on the parameter of the first quantum circuit output from a quantum computer, generating a parameter of a second quantum circuit including a rotation gate by inserting the rotation gate between a plurality of unitary gates in the first quantum circuit, and outputting the parameter of the second quantum circuit;

a quantum computer, based on the parameter of the second quantum circuit output from a classical computer, executing quantum computation and outputting measurement results of this quantum computation; and a classical computer, based on the measurement results output from a quantum computer, the Hamiltonian, and a derivative function of the Hamiltonian, computing a derivative function of energy corresponding to the Hamiltonian and outputting the derivative function of energy, wherein the classical computer inserts a rotation gate $R^{\pm}_{a,\mu}$ expressed by Equation (1) below between a plurality of unitary gates in the first quantum circuit in order to compute the derivative function of energy for a ground state, or the classical computer inserts a rotation gate $R^{(s),+}_{a,\mu}$ expressed by Equation (2) below between a plurality of unitary gates in the first quantum circuit to compute the derivative function of energy for an excited state $$R_{a,\mu}^{\pm}=\exp(\pm i\pi P_{a,\mu}/4)$$

$$P_{a,\mu} \in \mathcal{P}$$

$$\mathcal{P}=\{I,X,Y,Z\}^{\otimes n} \qquad (1)$$

$$R_{a,\mu}^{(s),+}=\exp(i\pi P_{a,\mu}^{(s)}/4)$$

$$P_{a,\mu}^{(s)} \in \mathcal{P}$$

$$\mathcal{P}=\{I,X,Y,Z\}^{\otimes n} \qquad (2)$$

wherein a is an index from among indices a, b, c, ... used to discriminate between elements of a parameter vector of a quantum circuit, µ is an index used to discriminate between Pauli operators, s is an index to represent excited states, $\mathcal{P}$ is a Pauli operator collection, I, X, Y, and Z are Pauli operators, ⊗ is the Kronecker product symbol, and n is a natural number.

\* \* \* \* \*

UNITED STATES PATENT AND TRADEMARK OFFICE
CERTIFICATE OF CORRECTION

PATENT NO. : 12,009,063 B2  
APPLICATION NO. : 17/159954  
DATED : June 11, 2024  
INVENTOR(S) : Kosuke Mitarai et al.

Page 1 of 1

It is certified that error appears in the above-identified patent and that said Letters Patent is hereby corrected as shown below:

In the Claims

Column 26, Lines 18-19, Claim 3:
After "initial information of a parameter"
Delete "expressing".

Signed and Sealed this
Nineteenth Day of November, 2024

Katherine Kelly Vidal
*Director of the United States Patent and Trademark Office*